United States Patent [19]

Covey et al.

[11] Patent Number: 5,776,959
[45] Date of Patent: Jul. 7, 1998

[54] ANTICONVULSANT AND ANXIOLYTIC LACTAM AND THIOLACTAM DERIVATIVES

[75] Inventors: Douglas F. Covey, Ballwin; P. Amruta Reddy; James A. Ferrendelli, both of Clayton, all of Mo.

[73] Assignee: Washington University, St. Louis, Mo.

[21] Appl. No.: 462,102

[22] Filed: Jun. 5, 1995

[51] Int. Cl.[6] ................................................ A01N 43/40
[52] U.S. Cl. ........................... 514/345; 546/216; 546/243
[58] Field of Search ................................ 546/216, 243; 548/543; 514/345

[56] References Cited

U.S. PATENT DOCUMENTS

| | | | |
|---|---|---|---|
| 3,228,955 | 1/1966 | Hickner et al. | 548/229 |
| 3,278,526 | 10/1966 | Louthan et al. | 540/526 |
| 3,306,910 | 2/1967 | Louthan et al. | 548/543 |
| 3,346,566 | 10/1967 | Chiddix et al. | 540/533 |
| 3,454,558 | 7/1969 | Stahl et al. | 540/485 |
| 3,531,471 | 9/1970 | Hartwimmer et al. | 540/451 |
| 3,536,699 | 10/1970 | Brachel et al. | 540/451 |
| 3,634,346 | 1/1972 | McKeon et al. | 540/532 |
| 3,754,088 | 8/1973 | Witzel | 514/315 |
| 4,198,514 | 4/1980 | Imanishi et al. | 546/216 |
| 4,707,491 | 11/1987 | Covey et al. | 514/445 |
| 5,010,079 | 4/1991 | Manoury et al. | 514/253 |

FOREIGN PATENT DOCUMENTS

| | | |
|---|---|---|
| 0151964 A2 | 8/1985 | European Pat. Off. . |
| 0 435 387 A1 | 7/1991 | European Pat. Off. . |
| 1527707 | 7/1968 | France . |
| 1527736 | 7/1968 | France . |
| 1527755 | 7/1968 | France . |

OTHER PUBLICATIONS

Laycock, G.M. et al, Nature, 1963, 200, pp. 849–851.

Jackman, L.M. et al, J. Org. Chem. 1982, 47, pp. 1824–1831.

Callery, P.S. et al, "Biosynthesis of 5–Aminopentanoic Acid and 2–Piperidone from Cadaverine and 1–Piperidone in Mouse" J. Neurochem. 1984, 43(6), pp. 1631–1634, abstract only.

Levine et al., "Alkyl–Substituted Thiolo–, Thiono–, and Dithio–γ–butyrolactones: New Classes of Convulsant and Anticonvulsant Agents," *J. of Med.Chem.* 29, 1986, 1996–1999.

Ferrendelli et al., "Comparison of the Anticonvulsant Activities of Ethosuximide, Valproate, and a New Anticonvulsant, Thiobutyrolactone," *Epilepsia*, 30(5):617–622., 1989, 617–622.

Holland et al., "Binding Interactions of Convulsant and Anticonvulsant γ–Butyrolactones and γ–Thiobutyrolactones with the Picrotoxin Receptor[1]," *J. of Pharmac. and Exp. Therapeutics*, 254, No. 2, 1990., 578–583.

Holland et al., "Physiological Regulation of the Picrotoxin Receptor by γ–Butyrolactones and γ–Thiobutyrolactones in Cultured Hippocampal Neurons," *J. of Neurosci.,* 10(6), 1990, 1719–1727.

Holland et al., "γ–Butyrolactone Antagonism of the Picrotoxin Receptor: Comparison of a Pure Antagonist and a Mixed Antagonist/Inverse Agonist," *Molecular Pharmacology*, 39:79–84, 1990.

Yoon, Kong–Woo et al., "Modulation of the Picrotoxin Receptor by Fluorinated Ethyl, Methyl–Butyrolactones[1]," *J. of Pharmac. and Experimantal Therapeutics*, 255, No. 1, 1990, 248–255.

Canney et al., "Synthesis and Structure–Activity Studies of Alkyl–Substituted γ–Butyrolactones and γ–Thiobutyrolactones: Ligands for the Picrotoxin Receptor," *J. of Med. Chem.*, 34, 1991, 1460–1467.

Holland et al., "Relative Anticonvulsant Effects of GABAmimetic and GABA Modulatory Agents," *Epilepsia*, 33(6):981–986, 1992.

Klunk et al., "Structure–Activity Relationships of Alkyl–Substituted γButyrolactones and Succinimides," *Molecular Pharm.*, 22:444–450, 1982.

Baker et al., "The Synthesis of 3,3–Diethylpiperid–2–one," *J.Amer.Chem.Soc.*, (C), 1967, 2148.

Menezea et al., "A Mild and Facile Route to ω–Amino Esters," *Synth. Comm.*, 18(14), 1988, 1625–1636.

Khoukhi et al., "Synthesis and Reactivity of Methyl γ–Azido Butyrates and Ethyl δ–Azido Valerates and of the Corresponding Acid Chlories As Useful Reagents for the Amionoalkylation," *Tetrahedron*, 43, No. 8, 1987, 1811–1822.

Adams et al., "The Absolute configuration of the $C^1$ Atom in Retronecanone (1–Methyl–7–oxopyrrolizidine)," vol. 81, Sep. 20, 1959.

Kametani et al., "The Alkaloids of *Corydalis pallida* var. tenuis (Yatabe) and the Structures of Pallidine and Kikemanine," *J.Amer.Chem.Soc.*, (C) 1970, 1060–1064.

Cummings et al., "The Synthesis and Rearrangement of 3–Vinyl–2–pyrrolidone," British Nylon Spinners Ltd., Research Department, Pontypool, Monmouthsire, UK, 1963, 4591–4604.

Geurtis et al., "2–Pyrrolidinones," *Chem.Abst.*, vol. 86, 1977, p.350.

Sinnreich et al., "The Light–Induced Addition of 2–Pyrrolidone To Olefins," *Tetrahedron*, vol. 24, 1968, 4509–4516.

Bentz et al., "Intramolecular Radical Trapping In Set Ring Opening of N–Enoyl Aziridines. A New Mechanistic Probe and A New Synthesis of Pyrrolidones," Tetrahedron Lett., vol. 28,No. 22, 1987, 2511–2512.

Werry et al., "Homolytic Aziridine Opening (Aza Variant of Cyclopropylcarbinyl–Homoallyl Rearrangement) By Addition of Tributyltin Radical to N–Acylaziridines. Factors Contributing To The Regioselectivity[1]," *Tetrahedron*, vol. 45, No. 16, 1989, 5015–5028.

(List continued on next page.)

*Primary Examiner*—C. Warren Ivy
*Assistant Examiner*—Garth M. Dahlen
*Attorney, Agent, or Firm*—Greenlee, Winner & Sullivan, P.C.

[57] ABSTRACT

This invention relates to lactam and thiolactam derivatives having useful anticonvulsant and anxiolytic activity, pharmaceutical compositions containing these compounds and therapeutic applications using such compositions.

49 Claims, No Drawings

OTHER PUBLICATIONS

Stamm et al., "Einstufensynthese von Pyrrolidonen durch Amidoethylierung einfacher Ester mit N–Acylaziridinen," *Chem. Ber.* 114, 1981, 32–48.

Kricheldorf, H.R., Reaktionen mit Silylaziden, 7, *Die Makromolekulare Chemic*, 176, 1975, 57–79.

Koelsch, C.F. "A Synthesis of 3–Alkylpiperidones," vol. 65, 2093, 1943.

Rodriguez et al., "Carba" peptide bond surrogates. Different approaches to Gly–ψ(CH$_2$–CH$_2$)–D.L–Xaa pseudo–dipeptide units. *Int.J.Peptide Protein Res.*, 39, 1992, 273–277.

Wang et al., "Fluorescent polarization immunoassay utilizing substituted triazinylaminofluoresceins," *Chem.Abst.*, vol. 100, 1984, p. 290.

Bodine et al., "An Efficient Conversion of N–Alkyllactams to N–Alkylthiolactams[1]," *Syn. Communications*, 12(10), 1982, 787–793.

Potts et al., "Intramolecular 1,4–Dipolar Cycloaddition of Cross–Conjugated Heterocyclic Betaines. A New Route to Hexahydrojulolidines and Related Peri–Fused Ring Systems," *J. Org. Chem.* 58, 1993, 5040–5042.

Lion et al., "Alkylation de Quelques Composés Carbonylés Par Des Groupes Teritiaires, Utilisation de la Réaction de Friedel–Crafts Dans La Syntheése D Ésters et de Cétones Encombrés," *Tetrahedron*, vol. 37, 1981, 319–323.

Spencer et al., "Ynenol Lactones: Synthesis and Investigation of Reactions Relevant to Their Inactivation of Serine Proteases," *J. Am. Chem. Soc.*, 108, 1986, 5589–5597.

Colombo et al., "Chemoenzymatic Synthesis of the Enantiomers of Iopanoic Acid," *Tetrahedron: Asymmetry*, vol. 2, No. 10, 1991, 1021–1030.

Quast et al., "Synthese von 3,5,5-Trialkyl-3,5–dihydro–4H–1,2,3–triazol–4–onen[2])," *Liebigs Ann. Chem.* 1986, 1891–1899.

Yamaguchi et al., "A Direct Synthesis of [(tert–Butoxycarbonyl)methylidene]azacycloalkanes from N–Alkyl Lactams." *J. Org. Chem.* 50, 1985, 1975–1977.

Meyers et al., "Conformational Effects on the Regiochemical Metalation of C$_5$–C$_{13}$ N–Benzyllactams," *J. Am. Chem. Soc.* 109, 1987, 4405–4407.

Swinyard et al., "Experimental Detection, Quantification, and Evaluation of Anticonvulsants," *Antiepileptic Drugs*, Woodbury, Pentry and Pippenger, eds., Raven Press, NY 1982, 111–126.

Lister, R.G., "The use of a plus–maze to measure anxiety in the mouse," *Psychopharm.* 92:180–185, 1987.

Hamill et al., "Improved Patch–Clamp Techniques for High–Resolution Current Recording from Cells and Cell–Free Membrane Patches," Pflugers Arch. 391:85–100, 1981.

Porter et al., "Antiepileptic Drugs," Chapt. 23, Springer, Berlin, 331–349.

Trevor et al., "Sedative–Hypnotics," Chapt. 21, 306–319.

Loscher at al., "Strategies in antiepileptic drug development: is rational drug design superior to random screening and structural variation?" *Epilepsy Research*, 17, 1994, 95–134.

ANTICONVULSANT AND ANXIOLYTIC LACTAM AND THIOLACTAM DERIVATIVES

ACKNOWLEDGEMENT OF SUPPORT

The invention herein was made in part with government support under NIH grant NS14834. The United States Government has certain rights in this invention.

FIELD OF THE INVENTION

This invention relates to lactam and thiolactam derivatives having anticonvulsant and anxiolytic activity which are useful as therapeutic agents for the treatment or prevention of convulsant seizures and/or anxiety. More particularly, the invention relates to 3-substituted and 3,3-disubstituted 2-pyrrolidinones (α-substituted and α,α-disubstituted γ-butyrolactams), and 3-substituted and 3,3-disubstituted 2-piperidinones (α-substituted and α,α-disubstituted δ-valerolactams) and thiolactam analogs having these therapeutically useful properties.

BACKGROUND OF THE INVENTION

Convulsant seizures occur in various chronic central nervous system (CNS) disorders, particularly epilepsies. These seizures are generally correlated with abnormal and excessive EEG (electroencephalogram) discharges. A variety of drugs have been used for treatment of these seizures. Many of the older drugs are structurally related to phenobarbital, for example, the hydantoins, the deoxybarbiturates, the oxazolidinediones and the succinimides. More recently developed anticonvulsant compounds include the benzodiazepines, iminostilbenes, and valproic acid. (Porter R J, Meldrum B S (1992) "Antiepileptic drugs" *Basic & Clinical Pharmacology*, Katzung B G, Ed., Appleton & Lange, Norwalk, Conn., 5th Edition, pp.331–349.) Additional compounds, containing various types of chemical structures and having various pharmacological mechanisms of action are being developed because of their anticonvulsant activities. (Trevor A J, Way W L (1992) "Sedative-hypnotics" *Basic & Clinical Pharmacology*, Katzung B G, Ed., Appleton & Lange, Norwalk, Conn., 5th Edition, pp.306-319.)

Some drugs which have anticonvulsant activities are also useful for the relief of anxiety, i.e., as anxiolytic agents. In particular, the benzodiazepines are useful for this purpose. These drugs can be used to ameliorate both situational anxiety and certain disease-associated anxiety conditions. Anxiolytic agents, having sedative-hypnotic actions are also widely used for the treatment of insomnia. (Loscher W, Schmidt D (1994) "Strategies in antiepileptic drug development: Is rational drug design superior to random screening and structural variation" *Epilepsy Res.*, 17, 95–134.)

The pharmacological mechanisms of actions of anticonvulsant and anxiolytic drugs are complex. One pharmacological mechanism of action of these agents is the ability to enhance the action of γ-aminobutyric acid (GABA), the major inhibitory neurotransmitter in the mammalian CNS, at $GABA_A$ receptors. The anticonvulsant and/or anxiolytic activities of clinically-useful drugs including benzodiazepines and barbiturates are correlated with their enhancement of this GABAergic activity. (Porter R J, Meldrum B S (1992) supra; Trevor A J, Way W L (1992) supra; Loscher W, Schmidt D (1994) supra.) Potentiation or enhancement of GABA function is assessed, for example, by measuring chloride ion current enhancement in cultured rat hippocampal and spinal cord neurons.

Analogs of α-alkyl substitued γ-butyrolactones and α-alkyl substituted γ-thiobutyrolactones are reported to have anticonvulsant activity. The thiobutyrolactones are reported to be more active than the butyrolactone analogs, with α-ethyl-α-methyl-γ-thiobutyrolactone reported to have the strongest activity. (Levine J A, Ferrendelli J A, Covey D F (1986) "Alkyl-substituted thiolo-, thiono-, and dithio-γ-butyrolactones: New classes of convulsant and anticonvulsant agents" *J. Med. Chem.*, 29, 1996–1999; Ferrendelli J A, Holland K D, McKeon A C, Covey D F (1989) "Comparison of the anticonvulsant activities of ethosuximide, valproate, and a new anticonvulsant, thiobutyrolactone" *Epilepsia*, 30, 617–622; Holland K D, McKeon A C, Covey D F, Ferrendelli J A (1990) "Binding interactions of convulsant and anticonvulsant γ-butyrolactones and γ-thiobutyrolactones with the picrotoxin receptor" *J. Pharmacol. Exp. Ther.*, 254, 578–583; Holland K D, Ferrendelli J A, Covey D F, Rothman S M (1990) "Physiological regulation of the picrotoxin receptor by γ-butyrolactones and γ-thiobutyrolactones in cultured hippocampal neurons" *J. Neuroscience*, 10, 1719–1727; Holland K D, Yoon K-W, Ferrendelli J A, Covey D F, Rothman S M (1991) "γ-Butyrolactone antagonism of the picrotoxin receptor: Comparison of a pure antagonist and a mixed antagonist/inverse agonist" *Mol. Pharmacol.*, 39, 79–84; Yoon K-W, Canney D J, Covey D F, Rothman S M (1990) "Modulation of the picrotoxin receptor by fluorinated ethyl, methyl-butyrolactones" *J. Pharmacol. Exp. Ther.*, 255, 248–255; Canney D J, Holland K D, Levine J A, McKeon A C, Ferrendelli J A, Covey D F (1991) "Synthesis and structure-activity studies of alkyl-substituted γ-butyrolactones and γ-thiobutyrolactones: ligands for the picrotoxin receptor" *J. Med. Chem.*, 34, 1460–1467; Holland K D, McKeon A C, Canney D J, Covey D F, Ferrendelli J A (1992) "Relative anticonvulsant effects of GABAmimetic and GABA modulatory agents" *Epilepsia*, 33, 981–986; Holland K D, Bouley M G, Covey D F, Ferrendelli J A (1993) "Alkyl-substituted γ-butyrolactones act at a distinct site allosterically linked to the TBPS/picrotoxinin site on the $GABA_A$ receptor complex" *Brain Res.*, 615, 170–174.)

EP patent application 151,964 (Tessitore P T, published 1985) reports α-amino-γ-butyrolactone derivatives, for example α-n-butylcarbonyl-amino-γ-butyrolactone, having anticonvulsant, anti-epileptic, sedative action and ability to inhibit the ingestion of alcohol.

U.S. Pat. No. 5,010,079 (Masoury P et al., issued Apr. 23, 1991) reports indolone derivatives useful in the treatment of anxiety, depression and schizophrenia.

In contrast to the properties of the lactones and thiolactones discussed above, 3,3-dimethyl-2-pyrrolidinone (α,α-dimethyl-γ-butyrolactam) was reported to display no anticonvulsant activity and 4-ethyl-4-methyl-2-pyrrolidinone (β-ethyl-β-methyl-γ-butyrolactam) was reported to be "much less active" by the convulsant and anticonvulsant criteria used compared to lactone analogs. (Klunk W E, Covey D F, Ferrendelli J A (1982) "Structure-Activity Relationships of Alkyl-Substituted γ-Butyrolactones and Succinimides" Mol. Pharmacol. 22 p. 444–450). Further, 3,3-Diethyl-2-piperidinone was reported to have weak sedative activity, a property undesirable in anticonvulsants and anxiolytics, in mice at a dose of 100 mg/kg. (Baker J A and Harper J F (1967) "The Synthesis of 3,3-Diethylpiperid-2-one" J. Chem. Soc. (C) p. 2148)

This invention is based in part on the inventors' finding that certain 3-mono- and 3,3-disubstituted lactams, in contrast to the reported lack of function in a 3,3-dimethyl lactam, do significantly enhance GABA neuronal inhibition and are significantly more active anticonvulsant and anxiolytic agents than prior art lactones and thiolactones. Further, these lactams have been found to have relatively low toxicity and low sedative activity.

Several 2-pyrrolidinone and 2-piperidinone derivatives have been reported:

3-methyl-2-pyrrolidinone (Menezes R, Smith M B (1988) "A mild and facile root to ω-amino esters" *Syn. Commun.*, 18, 1625–1636; Khoukhi N, Vaultier M, Carrie, R (1987) "Synthesis and reactivity of methyl γ-azidobutyrates and ethyl δ-azidovalerates and of the corresponding acid chlorides as useful reagents for the aminoalkylation" *Tetrahedron*, 43, 1811–1822; Adams R, Fles D (1959) "The absolute configuration of the C1 atom in retronecanone (1-methyl-7-oxopyrrolizidine" *J. Am. Chem. Soc.*, 81, 4946–4951.);

3-ethyl-2-pyrrolidinone (Kametani T, Ihara M, Honda T (1970) "Alkaloids of *Corydalis pallida var tenuis* and the structures of pallidine and kikemanine" *J. Chem. Soc. C*, 1060–1064; Cummings W A W, Davis A C (1964) "The synthesis and rearrangement of 3-vinyl-2-pyrrolidone" *J. Chem. Soc.*, 4591–4604; Brunner O, Heck-Bleckmann Chr (1951) "Uber das 3-athylpyrrolidin und einige derivate" *Monatsh.*, 82, 371–376.);

3-(2-methylpropyl)-2-pyrrolidinone (Geurtis L H, Meyer P J N "2-Pyrrolidinones" Ger. Offen. 2,609,209 Sep. 16, 1976 and Chem. Abstr. (1977) 86, 29622r);

3-butyl-2-pyrrolidinone (Sinnerich J, Elad D (1968) "The light-induced addition of 2-pyrrolidinone to olefins" *Tetrahedron*, 24, 4509–4516);

3-phenylmethyl-2-pyrrolidinone; (Menezes R, Smith M B (1988) supra; Bentz G, Besbes N, Laurent A, Stamm H (1987) "Intramolecular radical trapping in SET ring opening of N-(enoyl)aziridines. A new mechanistic probe and a new synthesis of pyrrolidones" *Tetrahedron Lett.*, 28, 2511–2512; Werry J, Stamm H, Lin P Y, Falkenstein R, Gries S, Irngartnger H (1989) "Reactions with aziridines. Part 50. Homolytic aziridine ring opening (aza variant of cyclopropylcarbinyl-homoallyl rearrangement) by addition of tributyltin radical to N-acylaziridines. Factors contributing to the regioselectivity" *Tetrahedron*, 45, 5015–5028); and 3,3-dimethyl-2-pyrrolidinone (Stamm H, Woderer A, Wiesert W (1981) "Reactions with aziridines. XXII. One step synthesis of pyrrolidones by amidoethylation of simple esters with N-acylaziridines" *Chem. Ber.*, 114, 32–48; Kricheldorf H R (1975) "Reactions with silylazides. 7. Trimethylsilyl 4-isocyanato-carboxylates and 4-aminocarboxylic acid N-carboxylic acid anhydrides" *Makromol. Chem.*, 176, 57–79.)

2-Piperidinone derivatives previously reported are as follows:

3-methyl-2-piperidinone (Khoukhi N, Vaultier M, Carrie, R (1987) supra); 3-ethyl-2-piperidinone (Koelsch C F (1943) "Synthesis of 3-alkylpiperidones" *J. Am. Chem. Soc.*, 65, 2458–2459); 3-propyl-2-piperidinone (Wang C H J, Stroupe S D, Jolley M E "Fluorescent polarization immunoassay utilizing substituted triazinylaminofluoresceins" U.S. Pat. No. 4,420,568 Dec. 13, 1983); 3-(2-methylpropyl) -2-piperidinone (Rodriguez M, Heitz A, Martinez J (1992) "'Carba' peptide bond surrogates. Different approaches to Gly-(CH2-CH2)-D,L-Xaa pseudo-dipeptide units" *Int. J. Peptide Protein Res.* 39, 273–277); 3-phenylmethyl-2-piperidinone; (Id.; Carter P A, Singh S "Preparation of di- and trisubstituted piperidines, morpholines, and bromopiperidines as agrochemical fungicides" Eur. Pat. Appl. EP 435,387. Jul. 3, 1991.); 3,3-dimethyl-2-piperidinone (Mileo J C, Sillion B, De Gaudemaris G. "3,3-Dimethyl-2-piperidinone" Fr. 1,527,755, Jun. 7, 1968); and 3,3-diethyl-2-piperidinone-(Baker J A, Harper J F (1967) "Synthesis of 3,3-diethylpiperid-2-one" *J. Chem. Soc., C*, 2148.)

EP patent application 435,387 (Carter P A and Singh S, published 1991) reports the formula:

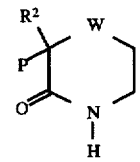

where W is —CH$_2$— or —CH$_2$—CH$_2$—, P is —CH$_2$—R$^1$ or —CH$_2$—CH$_2$—R$^1$ and where R$^2$ represents a hydrogen or an optionally substituted alkyl group and R$^1$ represents optionally substituted alkyl, phenyl, benzyl, or cycloalkyl group as potential intermediates in the synthesis of piperidine derivatives that are useful as fungicides.

All of the references cited in this specification are incorporated in their entirety by reference herein.

None of these 2-pyrrolidinone or 2-piperidinone derivatives were reported to enhance GABA-mediated chloride currents at GABA$_A$ receptors or to have anticonvulsant or anxiolytic activity.

SUMMARY OF THE INVENTION

This invention relates to lactam and thiolactam derivatives having useful anticonvulsant and anxiolytic activity, pharmaceutical compositions containing these compounds and therapeutic applications using such compositions.

In one aspect, the invention relates to compounds of formula I:

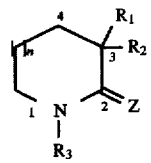

and any pharmaceutically acceptable salts thereof where:
n is 0 or 1; Z is an oxygen or a sulfur atom; and
R$_1$, R$_2$, and R$_3$, independently of one another, are selected from the group consisting of a hydrogen, an optionally substituted alkyl or alkenyl group, and an optionally substituted phenylmethyl group;
with the exceptions that:
R$_1$ and R$_2$ cannot both be a hydrogen; and
when one of R$_1$ or R$_2$ is a hydrogen or a methyl group, the other of R$_1$ or R$_2$ cannot be a methyl or ethyl group.

In a second aspect, this invention relates to compounds of formula II:

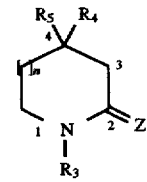

and any pharmaceutically acceptable salts thereof where:
n is 0 or 1; Z is an oxygen or a sulfur atom; and
R$_4$, R$_5$, and R$_3$, independently of one another, are selected from the group consisting of a hydrogen, an optionally substituted alkyl or alkenyl group, and an optionally substituted phenylmethyl group;

with the exceptions that:

$R_4$ and $R_5$ cannot both be a hydrogen; and when one of $R_4$ or $R_5$ is a hydrogen or a methyl group, the other of $R_4$ or $R_5$ cannot be a methyl or ethyl group.

Compounds of formulas I and II, alone or in combination with each other and/or an appropriate pharmaceutical carrier are useful in the preparation of pharmaceutical compositions having anti-convulsive and anxiolytic activity in mammals. These compounds alone or in combination with each other enhance GABA-induced chloride currents at the GABA receptor/chloride ionophore complex of mammals. These compounds alone or in combination with each other are useful for treating any disorders which can be ameliorated by increasing neuronal inhibition, particularly via GABA-induced chloride current modulation. These compounds, alone or in combination, have utility as anxiolytics and/or anti-convulsants. These compounds alone or in combination with each other are useful in preventing or ameliorating convulsant seizures and/or useful in preventing or ameliorating anxiety in mammals.

Compounds which enhance GABAergic function are useful in the treatment of pre-menstrual syndrome (PMS). Thus, compounds of this invention, like those of formulas I and II, alone or in combination are useful in the treatment of PMS.

This invention includes pharmaceutical compositions comprising any of the compounds of formulas I and II, alone or in combination with each other, in an amount effective for ameliorating convulsions or the symptoms of convulsions or in an amount effective for ameliorating anxiety or its symptoms. Pharmaceutical compositions of this invention include various pharmaceutical dosage forms formulated for oral or transdermal administration or administration by injection to a mammal and include among others, tablets, pills, capsules, and injectable solutions or suspensions. Pharmaceutical compositions of this invention contain from about 0.1% to about 99% of one or more compounds of formula I or II. The inventive pharmaceutical compositions include those that contain from about 1% to about 90% of one or more of the compounds of formula I or II.

This invention is also directed to methods of enhancing GABA-induced chloride currents at the GABA receptor/chloride ionophore complex in a mammal by administration of an anticonvulsant or anxiolytic compound of formula I or II, or mixtures thereof, the compound or mixture of compounds being administered in an amount effective for enhancement of the GABA-induced chloride current.

This invention is also directed to methods of preventing or treating convulsant seizures in mammals, by administration to the mammal of an amount of a compound of formula I or II effective for preventing or ameliorating convulsant seizures or the symptoms of such seizures. This invention is further directed to methods of preventing or treating anxiety in mammals by administration to the mammal of an amount of a compound of formula I or II or mixtures thereof effective for preventing or ameliorating anxiety or the symptoms of anxiety. Administration can be by any known route including, but not limited to, injection or oral or transdermal routes.

This invention also includes novel compounds of formula I and II which have anticonvulsant and/or anxiolytic activity. In particular novel anticonvulsant and/or anxiolytic compounds of this invention include compounds of formula I and any pharmaceutically acceptable salts thereof wherein:

n is 0 or 1; Z is oxygen or sulfur;

$R_1$, $R_2$ and $R_3$, independently of one another, are selected from the group consisting of a hydrogen, an optionally substituted alkyl or alkenyl group, and an optionally substituted phenylmethyl group;

with the exceptions that:

$R_1$ and $R_2$ cannot both be a hydrogen; and when one of $R_1$ or $R_2$ is a hydrogen or a methyl group, the other of $R_1$ or $R_2$ cannot be a methyl or ethyl group;

when $R_3$ is a hydrogen and one of $R_1$ or $R_2$ is a hydrogen, the other of $R_1$ or $R_2$ must be a substituted alkyl, substituted alkenyl or substituted phenyl methyl group;

and further excluding:

3-phenylmethyl-2-pyrrolidionone, 3,3-diethyl-2-piperidinone, and 3-phenylmethyl-2-piperidinone.

This invention also includes novel compounds of formula II having anticonvulsive and/or anxiolytic activity.

The anticonvulsive and/or anxiolytic lactam compounds of this invention are superior to prior art lactones and thiolactones because the lactams display significantly more potent anticonvulsant and anxiolytic activity, significantly less neurotoxicity, and have significant advantageous pharmaceutical properties, including enhanced water solubility, lack of unpleasant odor, and solid form at ambient temperatures normally encountered by warm blooded animals, when compared to prior art compounds.

DETAILED DESCRIPTION OF THE INVENTION

Anticonvulsant and/or anxiolytic compounds of this invention are lactams and thiolactams which can be described by the general formula:

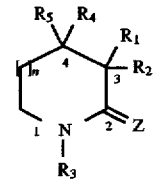

where n, Z, $R_1$, $R_2$, $R_3$, $R_4$, and $R_5$ are as defined in formulae I and II above except that $R_4$ and $R_5$ must both be hydrogens if one of $R_1$ or $R_2$ is not a hydrogen and that $R_1$ and $R_2$ must both be hydrogens if one of $R_4$ or $R_5$ is not a hydrogen, i.e., there cannot be substituents other than hydrogen at both the 3 and 4 ring positions.

Anticonvulsant and/or anxiolytic compounds of formual I of this invention include lactams (formula III) and thiolactams (formula IV) where n, $R_1$, $R_2$, and $R_3$ are as defined for formula I.

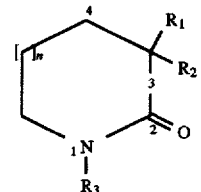

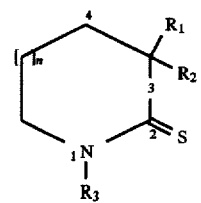

where lactams of formula III are generally preferred over thiolactams of formula IV.

Compounds of formula I include both five- and six-member ring compounds which are exemplified by pyrrolidinones of formula V and piperidinones of formula VI:

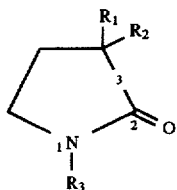

V

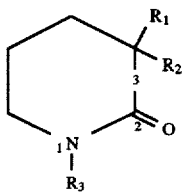

VI where $R_1$, $R_2$, and $R_3$ are as defined above for formual I.

In specific aspects, this invention includes compounds of formula I and II where one of $R_1$ or $R_2$ or one of $R_4$ or $R_5$ is an optionally substituted phenylmethyl group as exemplified in the lactams and thiolactams of formula VII and VIII:

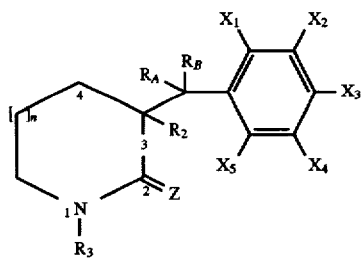

VII

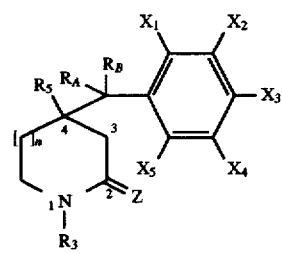

VIII where n, Z, $R_1$, $R_5$ and $R_3$ are as defined above for formulae I and II and $R_A$, $R_B$, $X_1$, $X_2$, $X_3$, $X_4$ and $X_5$ are hydrogens or substitutents, as defined below.

In formulas I-VIII, one or more of $R_1$, $R_2$, $R_3$, $R_4$, and $R_5$ can be optionally substituted alkyl, alkenyl or phenylmethyl groups. Substitutents include, among others, halogen atoms, a carbonyl, cyano, hydroxy, mercapto, amino or nitro group, alkynyl, alkoxy, thioalkoxy, alkyl amine, haloalkyl or haloalkenyl group, particularly those substituents having up to about 6 carbon atoms, and preferably those substituents having from one to about 4 carbon atoms and alkyl, alkenyl or alkynyl groups substituted with one or more carbonyl, cyano, hydroxy, mercapto, amino or nitro groups, particularly those substituents having up to about 6 carbon atoms and preferably those substituents having from 1 to about 4 carbon atoms. Preferred halogen substituents are fluorines and preferred haloalkyl and haloalkenyl groups are fluoroalkyl and fluoroalkenyl groups, respectively, e.g., —$CH_2F$, —$CHF_2$, —$CH_2$—$CF_3$, and —$CH$=$CF_2$. Fluoroalkyl and fluoroalkenyl groups include those that are perfluorinated, e.g., —$CF_3$, —$CF_2$—$CF_3$, and —$CF$=$CF_2$.

Optionally substituted alkyl and alkenyl groups of $R_1$, $R_2$, $R_3$, $R_4$, and $R_5$ include those which are straight-chain, branched or contain an alicyclic group, e.g., cyclopropyl, cyclobutyl, cyclohexyl, perfluoroalicyclic groups and the like.

Optionally substituted alkyl and alkenyl groups include haloalkyl and haloalkenyl groups, particularly those having from 1 to about 4 carbon atoms. Preferred haloalkyl groups and haloalkenyl groups are fluoroalkyl and fluoroalkenyl groups, respectively.

As illustrated in formulas VII and VIII, phenylmethyl groups can be substituted at the methyl carbon or on the phenyl ring. For optionally substituted phenylmethyl groups of any of $R_1$, $R_2$, $R_3$, $R_4$ and $R_5$, substituents include halogen atoms, a carbonyl, cyano, hydroxy, mercapto, amino or nitro group, an alkyl, alkenyl, alkynyl, alkoxy, thioalkoxy, alkyl amine, haloalkyl or haloalkenyl group, particularly those groups having up to about 6 carbon atoms, perferably those groups having 1 to 4 carbon atoms and alkyl or alkenyl groups substituted with one or more carbonyl, cyano, hydroxy, mercapto, amino or nitro groups, particularly those groups having up to about 6 carbon atoms and preferably those having 1 to 4 carbon atoms. Generally preferred substituents for $R_1$, $R_2$, $R_3$, $R_4$ and $R_5$ groups are atoms or chemical moieties or groups that do not interfere with anticonvulsant or anxiolytic activity of the compound.

More specfically with respect to phenylmethyl group substituents and particularly substituents $R_A$, $R_B$, $X_1$, $X_2$, $X_3$, $X_4$ and $X_5$, these substituents, independently of one another, can, for example, be selected from the group consisting of a hydrogen, a halogen, an alkyl, an alkenyl, an alkoxy, an alkylamino, a mercapto, a thioalkyl, a thioalkoxy, a haloalkoxy, a haloalkenyl, a hydroxy, an amino, a nitro or a cyano group. Substituents include those having up to about 6 carbon atoms, particularly alkyl or alkenyl groups. Generally preferred substituents are those having from one to about 4 carbon atoms, particularly alkyl and alkenyl groups.

The substituents on the phenylmethyl group are illustrated by one or more of the following groups in any of the ortho-, meta- or para-positions of the phenyl ring and/or at either or both positions on the methyl carbon: F, Cl, Br, I, acetyl, alkyl (C1 to about C4), alkenyl (C1 to about C4), alkynyl (C1 to about C4), alkoxyl (C1 to about C4), haloalkyl (C1 to about C4), haloalkenyl (C1 to about C4), amino, mono- and dialkylamino (C1 to about C4), cyano, hydroxy, mercapto, nitro, and carboxy.

Preferred haloalkyl and haloalkenyl substituents for phenylmethyl groups are fluoroalkyl and fluoroalkenyl groups having up to about 4 carbon atoms. Generally preferred substituents for phenylmethyl groups are fluorines and small alkyl or alkenyl groups having from 1 to about 4 carbon atoms. The phenyl ring of the phenylmethyl group can be substituted at any position.

Alkyl substituents in the above structural formulae are illustrated by methyl, ethyl, propyl, isopropyl, iso-butyl, sec-butyl, and tert-butyl, cyclopropyl and cyclobutyl. The fluoroalkyl substituents are illustrated by trifluoromethyl, 1,1-difluoroethyl, 2,2,2-trifluoroethyl, 1-trifluoromethylethyl, and 1-methyl-1-trifluoromethylethyl.

When the $R_1$ and $R_2$ or $R_4$ and $R_5$ substituents are different, the compounds of the above structural formulae (I-VIII) exist as (+)- and (−)-enantiomers. Such compounds of this invention are useful either in the racemic (+/−)-form or the nonracemic (+)- or (−)-enantiomeric forms.

Anticonvulsant and/or anxiolytic compounds of this invention include those of the above formulae in which $R_3$ is selected from the group consisting of a hydrogen, an alkyl or alkenyl group having from one to about 6 carbon atoms and a phenylmethyl or an optionally substituted phenylmethyl group. Also included are those compounds in which $R_3$ is an alkyl or alkenyl group having from one to about four carbon atoms, those where $R_3$ is a hydrogen, methyl or ethyl group, those where $R_3$ is a phenylmethyl group and those where $R_3$ is a hydrogen.

Anticonvulsant and/or anxiolytic compounds of this invention specifically include those where Z is oxygen. In particular, this invention includes 3-mono- and 3,3-disubstituted and 4-mono- and 4,4-disubstituted 2-pyrrolidinones, where Z is oxygen and n=0 and and 3-mono and 3,3-disubstituted and 4-mono and 4,4-disubstituted 2-piperidinones, where Z is oxygen and n=1 with the $R_1$, $R_2$, $R_3$, $R_4$ and $R_5$ substitutents listed above in formulae I and II.

Anticonvulsant and/or anxiolytic compounds of this invention include those in which $R_1$ is a different group from $R_2$ and those in which $R_4$ is a different group from $R_5$.

Anticonvulsant and/or anxiolytic compounds of this invention include those compounds of formula I in which one of $R_1$ or $R_2$ is a phenylmethyl or substituted phenylmethyl group. Also included are those compounds where one of $R_1$ or $R_2$ is a phenylmethyl or substituted phenylmethyl group and the other is a hydrogen or an alkyl having from 2 to about 4 carbon atoms.

Preferred anticonvulsant and/or anxiolytic compounds of formula I are those in which $R_1$ and $R_2$ are selected from the group consisting of a hydrogen, an alkyl or alkenyl having two to about four carbon atoms and a phenylmethyl group. Also preferred are those in which $R_3$ is a hydrogen, methyl, ethyl or phenylmethyl group. More preferred $R_3$ groups are those having two or fewer carbon atoms.

Anticonvulsant and/or anxiolytic compounds of this invention include those compounds of formula II in which one of $R_4$ or $R_5$ is a phenylmethyl or substituted phenylmethyl group. Also included are those compounds where one of $R_4$ or $R_5$ is a phenylmethyl or substituted phenylmethyl group and the other is a hydrogen or an alkyl having from 2 to about 4 carbon atoms.

Preferred anticonvulsant and/or anxiolytic compounds of formula II are those in which $R_4$ and $R_5$ are selected from the group consisting of a hydrogen, an alkyl or alkenyl having two to about four carbon atoms and a phenyl methyl group. Also perferred are those in which $R_3$ is a hydrogen, methyl, ethyl or phenylmethyl group. More preferred $R_3$ are those having two or fewer carbon atoms.

Representative anticonvulsant and/or anxiolytic compounds of this invention are 3,3-diethyl-2-pyrrolidinone, 3-ethyl-3-phenylmethyl-2-pyrrolidinone, 3-methyl-3-phenylmethyl-2-pyrrolidinone, 3-phenylmethyl-2-pyrrolidinone, 3,3-diethyl-2-piperidinone, 3-ethyl-3-phenylmethyl-2-piperidinone, 3-methyl-3-phenylmethyl-2-piperidinone and 3-phenylmethyl-2-piperidinone, 3-ethyl-3-isopropyl-2-pyrrolidinone; 3-ethyl-3-iso-propyl-2-piperidinone; 3-isopropyl-3-phenylethyl-2-piperidinone; 3-ethyl-3-methyl-2-piperidinone.

Additional representative compounds of this invention include, among others:

3-(p-fluorophenylmethyl)-2-pyrrolidinone, 3-(p-fluorophenylmethyl)-2-piperidinone, 3-(p-fluorophenylmethyl)-3-methyl-2-pyrrolidinone, 3-(p-fluorophenylmethyl)-3-methyl-2-piperidinone;

3-n-propyl-2-pyrrolidinone, 3-isopropyl-2-pyrrolidinone, 3-tert-butyl-2-pyrrolidinone, 3-n-butyl-2-pyrrolidinone, 3-sec-butyl-2-pyrrolidinone, 3-n-propyl-2-piperidinone, 3-isopropyl-2-piperidinone, 3-tert-butyl-2-piperidinone, 3-n-butyl-2-piperidinone, 3-sec-butyl-2-piperidinone;

3,3-diethyl-1-methyl-2-pyrrolidinone, 3-ethyl-1-methyl-3-phenylmethyl-2-pyrrolidinone, 1,3-dimethyl-3-phenylmethyl-2-pyrrolidinone, 1-methyl-3-phenylmethyl-2-pyrrolidinone, 3,3-diethyl-1-methyl-2-piperidinone, 3-ethyl-1-methyl-3-phenylmethyl-2-piperidinone, 1,3-dimethyl-3-phenylmethyl-2-piperidinone, 1-methyl-3-phenylmethyl-2-piperidinone, 3-ethyl-1,3-dimethyl piperidinone;

3,3-diethyl-1-phenymethyl-2-pyrrolidinone, 1,3-diphenylmethyl-3-ethyl-2-pyrrolidinone, 1,3-diphenylmethyl-3-methyl-2-pyrrolidinone, 1,3-diphenylmethyl-2-pyrrolidinone, 3,3-diethyl-1-phenylmethyl-2-piperidinone, 1,3-diphenylmethyl-3-ethyl-2-piperidinone, 1,3-diphenylmethyl-3-methyl-2-piperidinone, 1,3-diphenylmethyl-2-piperidinone, 3-ethyl-3-methyl-1-phenylmethyl-2-piperidinone;

4,4-diethyl-2-pyrrolidinone, 4-ethyl-4-phenylmethyl-2-pyrrolidinone, 4-methyl-4-phenylmethyl-2-pyrrolidinone, 4-phenylmethyl-2-pyrrolidinone, 4,4-diethyl-2-piperidinone, 4-ethyl-4-phenylmethyl-2-piperidinone, 4-methyl-4-phenylmethyl-2-piperidinone and 4-phenylmethyl-2-piperidinone, 4-ethyl-4-isopropyl-2-pyrrolidinone; 4-ethyl-4-iso-propyl-2-piperidinone; 4-isopropyl-4-phenylethyl-2-piperidinone; 4-ethyl-4-methyl-2-piperidinone.

4,4-diethyl-1-phenymethyl-2-pyrrolidinone, 1,4-diphenylmethyl-4-ethyl-2-pyrrolidinone, 1,4-diphenylmethyl-4-methyl-2-pyrrolidinone, 1,4-diphenylmethyl-2-pyrrolidinone, 4,4-diethyl-1-phenylmethyl-2-piperidinone, 1,4-diphenylmethyl-4-ethyl-2-piperidinone, 1,4-diphenylmethyl-4-methyl-2-piperidinone, 1,4-diphenylmethyl-2-piperidinone, 4-ethyl-4-methyl-1-phenylmethyl-2-piperidinone;

3,3-diethyl-2-pyrrolidinethione, 3-ethyl-3-phenylmethyl-2-pyrrolidinethione, 3-methyl-3-phenylmethyl-2-pyrrolidinethione, 3-phenylmethyl-2-pyrrolidinethione, 3,3-diethyl-2-piperidinethione, 3-ethyl-3-phenylmethyl-2-piperidinethione, 3-methyl-3-phenylmethyl-2-piperidinethione, 3-phenylmethyl-2-piperidinethione.

4,4-diethyl-2-pyrrolidinethione, 4-ethyl-4-phenylmethyl-2-pyrrolidinethione, 4-methyl-4-phenylmethyl-2-pyrrolidinethione, 4-phenylmethyl-2-pyrrolidinethione, 4,4-diethyl-2-piperidinethione, 4-ethyl-4-phenylmethyl-2-piperidinethione, 4-methyl-4-phenylmethyl-2-piperidinethione, 4-phenylmethyl-2-piperidinethione Preferred compounds of this invention are 3,3-diethyl-2-pyrrolidinone, 3-ethyl-3-phenylmethyl-2-pyrrolidinone, 3-methyl-3-phenylmethyl-2-pyrrolidinone, 3-phenylmethyl-2-pyrrolidinone, 3,3-diethyl-2-piperidinone, 3-ethyl-3-phenylmethyl-2-piperidinone, 3-methyl-3-phenylmethyl-2-piperidinone, 3-phenylmethyl-2-piperidinone.

Pharmaceutical compositions of this invention are those having one or more of the compounds of formulae I–VIII in an amount effective for preventing convulsions and/or anxiety in a mammal. Preferred pharmaceutical compositions of this invention include those having one or more of the 3-mono and 3,3-disubstituted compounds of formula I in an amount effective for preventing convulsions and/or anxiety in a mammal.

Methods of synthesis of the compounds of formula I are illustrated by the methods of Schemes 1–4. Compounds of formula I including 5- and 6-member ring compounds of formulas III and IV, respectively, can be readily prepared following the guidance provided herein, using the methods described herein or routine modifications or adaptations thereof, or using synthetic methods well-known in the art. Compounds of formula II can be readily synthesized by those of ordinary skill in the art, in view of the guidance provided herein, and methods well-known in the art of organic synthesis. Synthetic methods described herein or well-known in the art can be readily modified and/or adapted, for example, by routine choice of starting materials, reaction conditions, reagents and/or purification methods to synthesize the compounds of formulas I-VIII.

The 2-pyrrolidinone derivatives of this invention can be prepared by various means. Schemes 1 and 2 show two methods which can be used to prepare these compounds. According to the method of scheme 1, an alkanoic ester $R_1R_2HCCOOR_3$ is converted into a β-cyano alkanoic ester after which the cyano group is reduced to an amino group which cyclizes in situ to yield a 3-substituted 2-pyrrolidinone. Alternatively, in the method of Scheme 2, a $CH_2=CHCH_2$— group is added to an alkanoic ester $R_1R_2HCCOOR_3$ and then the terminal carbon of the alkenyl group is removed to obtain an aldehyde group. The aldehyde group is converted to an oxime group which is then reduced to obtain an amino group which cyclizes in situ to yield a 2-pyrrolidinone derivative.

The synthesis of 2-piperidinone derivatives of this invention is illustrated in Scheme 3. A $CH_2=CHCH_2$— group is added to the ester $R_1R_2HCCOOR_3$ after which the alkenyl group is subjected to a hydroboration reaction which removes the double bond and adds a hydroxyl group to the terminal carbon. The hydroxyl group is then oxidized to an aldehyde group. The aldehyde is then converted into an oxime which is then reduced to an amino group. The resulting amine cyclizes in situ to yield a 2-piperidinone derivative.

Alternatively, N-benzylated 2-piperidinone ($R_1=H$) or a 3-monosubstituted 2-piperidinone ($R_1$=alkyl or other group) can be alkylated by standard procedures, and the N-benzyl group can be removed to obtain the desired 2-piperidinone derivatives as shown in Scheme 4.

Ester $R_1R_2HCCOOR_3$ starting materials for the preparation of compounds of formula I are either commercially available or can be readily prepared from commercially available materials using standard alkylation procedures such as those reported by Canney D J, Holland K D, Levine J A, McKeon A C, Ferrendelli J A, Covey D F (1991), supra or other well-known procedures. Substituents can be introduced into phenylmethyl $R_1$ or $R_2$ groups by choice of appropriate starting materials which are available commercially or through standard methods well-known in the art.

N-benzylated 2-piperidinone starting materials can be readily prepared from commercially available materials using well-known synthetic methods. It will be readily apparent to those of ordinary skill in the art that groups other than the benzyl group can be used to protect the N in the methods of Scheme 4.

Thiolactams can be prepared by treating the analogous lactams with either phosphorus pentasulfide or Lawesson's reagent, for example, by methods described in Bodine J J and Kaloustian M K (1982) "An Efficient Conversion of N-Alkyllactams to N-Alkylthiolactams" Synthetic Comm. 12(10) 787–793 and Potts K T, Rochanapruk T, Coats S J, Hadjiarapoglou L, and Padwa A (1993) "Intramolecular 1,4-Dipolar Cycloaddition of Cross-Conjugated Heterocyclic Betains. A New Route to Hexahydrojulolidines and Related Peri-Fused Ring Systems" J. Org. Chem. 58 5040–5042. Thiolactams of formula I can be prepared by these methods or by art-known modifications or adaptations thereof.

Compounds of formulae I and II with $R_1$, $R_2$, $R_3$, $R_4$ and $R_5$ that are hydrogens or optionally substituted alkyl, alkenyl or phenylmethyl groups can be readily synthesized by reference to methods disclosed herein as in view of methods well-known in the art. All these lactams and thiolactams and derivatives with various $R_1$, $R_2$, $R_3$, $R_4$ and $R_5$ as well as with any phenylmethyl group substitutents $R_A$, $R_B$, $X_1$, $X_2$, $X_3$, $X_4$, and $X_5$ can be readily synthesized using methods described herein in combination with well-known synthetic methods or routine modifications and adaptations of these methods.

The usefulness of the anticonvulsive and/or anxiolytic compounds of this invention (compounds of formulas I-VIII) for the treatment of convulsant seizures and anxiety is demonstrated by the data reported in Tables 2–4 for representative compounds.

As shown in Table 1, 3,3-diethyl-2-pyrrolidinone and 3-methyl-3-iso-propyl-2-pyrrolidinone enhance GABA-mediated chloride ion currents in cultured rat hippocampal neurons more effectively than the previously described α-ethyl-α-methyl-γ-thiobutyrolactone.

Table 2 demonstrates the activity of compounds of the invention to block either pentylenetetrazol (PTZ) or maximal electroshock (MES) seizures in mice. These tests are described in Example 14 and are employed to assess anticonvulsant activity of a given test compound. Compounds listed in Table 2 are compared to α-ethyl-α-methyl-γ-thiobutyrolactone, the thiolactone derivative that has been reported to be the most active in its ability to block these types of seizures.

For purposes of this application, compounds with useful anticonvulsant activity are defined as those compounds having $ED_{50}$ less than about 350 mg/kg as measured by the MES test or less than about 220 mg/kg as measured by the PTZ test. Compounds displaying $ED_{50}$ equal to or less than about 100 mg/kg (by PTZ) or equal to or less than 200 mg/kg (by MES) are generally preferred. Compounds displaying $ED_{50}$ equal to or less than about 50 mg/kg (by MES) or equal to or less than about 75 mg/kg (by PTZ) are generally more preferred.

The data of Table 2 also demonstrate that the more active 2-pyrrolidinones and 2-piperidinones are also generally less toxic than the α-ethyl-α-methyl-γ-thiobutyrolactone. This is particularly striking when toxicity is considered as the ratio of active dose ($ED_{50}/TD_{50}$). Anticonvulsant and/or anxiolytic compounds with higher $TD_{50}$ are generally preferred, those in which the ratio of $TD_{50}/ED_{50}$ (by PTZ or MES) is about 2 or more are generally more preferred and those in which the ratio $TD_{50}/ED_{50}$ (by PTZ or MES) is about 4 or more are generally more preferred.

The superior activity of compounds of this invention as anxiolytic agents is demonstrated by that of 3,3-diethyl-2-pyrrolidinone which has significantly stronger anxiolytic activity when compared to α-ethyl-α-methyl-γ-thiobutyrolactone in Table 3.

As indicated in Table 4, 2-pyrrolidinones having non-hydrogen substitution at both the 3 and 4 positions or at both the 3 and 5 positions or at the 5 position act as convulsants. Compounds of formula I and II having non-hydrogen substitution at both the 3 and 4 positions or at both the 3 and 5 positions or at the 5 position will act as convulsants.

In view of these results, lactams of formula I where $R_1$ and $R_2$ are both hydrogens; where $R_1$ and $R_2$ are both methyl groups; and where one of $R_1$ or $R_2$ is a hydrogen and the other of $R_1$ or $R_2$ is an alkyl group having less than three carbon atoms and 2-pyrrolidinones of formual I (where n=0 and Z is oxygen) where one of $R_1$ or $R_2$ is a methyl group and the other of $R_1$ or $R_2$ is an alkyl group having less than three carbon atoms will at most have weak anticonvulsant and/or anxiolytic activity not useful for therapeutic applications in mammals. Thiolactams of formula I will display similar relative activity as a function of $R_1$ and $R_2$ substitutions.

13

Further, in view of these results, lactams of formula II where $R_4$ and $R_5$ are both hydrogens; where $R_4$ and $R_5$ are both methyl groups; and where one of $R_4$ or $R_5$ is a hydrogen and the other of $R_4$ or $R_5$ is an alkyl group having less than three carbon atoms and 2-pyrrolidinones of formual II (where n=0 and Z is oxygen) where one of $R_4$ or $R_5$ is a methyl group and the other of $R_4$ or $R_5$ is an alkyl group having less than three carbon atoms will at most have weak anticonvulsant and/or anxiolytic activity not useful for therapeutic applications in mammals. Thiolactams of formula II will display similar relative activity as a function of $R_4$ and $R_5$ substitutions.

Based on the data in Table 2, alkyl substitution at the N (1-ring position, $R_3$) in the 2-pyrrolidinone has little effect on anticonvulsant and/or anxiolytic activity. In view of this result, alkyl substitution at $R_3$ in the compounds of formula I and II will have little or no detrimental effect on anticonvulsant and/or anxiolytic activity.

The compounds are formulated according to conventional methods, and may be administered systemically by injection subcutaneously, intravenously, or intraperitoneally, as well as by oral or transdermal administration. The formulations of pharmaceutical compositions containing these compounds will, of course, depend on the intended route of administration.

Table 1: Comparison of the Potentiation of GABA Currents in Cultured Rat Hippocampal Neurons by 2-Pyrrolidinone Derivatives and α-Ethyl-α-methyl-γ-thiobutyrolactone

| Compound[1] | % Potentiation Relative to Control (N)[2] |
|---|---|
| 3,3-diethyl-2-pyrrolidinone | 274 ± 64 (4) |
| 3-methyl-3-iso-propyl-2-pyrrolidinone | 265 ± 29 (5) |
| α-ethyl-α-methyl-γ-thiobutyrolactone | 170 ± 12 (12) |

[1]Concentration of compound 1 mM.
[2]Values represent mean ± SEM; results are expressed as percent of control response (100%) to 3µM GABA. N is the number of cells examined.

TABLE 2

Comparison of the Anticonvulsant Potencies and Toxicities of 2-Pyrrolidinone and 2-Piperidinone Derivatives and α-Ethyl-a-methyl-γ-thiobutyrolactone.

| Compound | Convulsant Challenge (ED$_{50}$, mg/kg) PTZ | MES | Toxicity (TD$_{50}$, mg/kg) |
|---|---|---|---|
| 3,3-Diethyl-2-pyrrolidinone | 46 | 174 | 260 |
| 3-Ethyl-3-phenylmethyl-2-pyrrolidinone | 42 | 74 | 126 |
| 3-Methyl-3-phenylmethyl-2-pyrrolidinone | 63 | 55 | 167 |
| 3-Phenylmethyl-2-pyrrolidinone | 71 | 41 | 144 |
| 3,3-Diethyl-2-piperidinone | 39 | 56 | 177 |
| 3-Ethyl-3-phenylmethyl-2-piperidinone | 61 | 79 | 102 |
| 3-Methyl-3-phenylmethyl-2-piperidinone | 56 | 49 | 131 |
| 3-Phenylmethyl-2-piperidinone | 85 | 42 | 294 |
| α-ethyl-α-methyl-γ-thiobutyrolactone | 128 | 209 | 244 |
| α,α-dimethyl-γ-thiobutyrolactone | >500 | Not Tested | Not Tested |
| 2-Pyrrolidinone | >900 | >600 | >900 |

14

TABLE 2-continued

Comparison of the Anticonvulsant Potencies and Toxicities of 2-Pyrrolidinone and 2-Piperidinone Derivatives and α-Ethyl-a-methyl-γ-thiobutyrolactone.

| Compound | Convulsant Challenge (ED$_{50}$, mg/kg) PTZ | MES | Toxicity (TD$_{50}$, mg/kg) |
|---|---|---|---|
| 3-Methyl-2-pyrrolidinone | >900 | >750 | ~900 |
| 3-Ethyl-2-pyrrolidinone | >750 | 535 | 260 |
| 3,3-Dimethyl-2-pyrrolidinone | 708 | >600 | 900 |
| 3-Ethyl-3-methyl-2-pyrrolidinone | 226 | 357 | 622 |
| 1,3-Dimethyl-3-ethyl-2-pyrrolidinone | 259 | Not Tested | 520 |
| 4,4-Dimethyl-2-pyrrolidinone | 600 | Not Tested | >600 |
| 4-Ethyl-4-Methyl-2-pyrrolidinone | 327 | >300 | >300 |
| 2-Piperidinone | >600 | Not Tested | >600 |
| 3-Methyl-2-Piperidinone | >600 | >600 | >600 |
| 3-Ethyl-2-Piperidinone | 339 | Not Tested | 382 |
| 3-Ethyl-3-Methyl-2-Piperidinone | 162 | 198 | 382 |

TABLE 3

Comparison of the Anxiolytic Potencies of 3,3-Diethyl-2-pyrrolidinone and α-Ethyl-α-methyl-γ-thiobutyrolactone

| Compound and Dose (mg/kg)[1] | Time spent on Plus-Maze Open Arms (% of Control)[2] |
|---|---|
| 3,3-diethyl-2-pyrrolidinone | |
| 100 (N = 13) | 179% (P < 0.02) |
| 175 (N = 14) | 253% (P < 0.01) |
| α-ethyl-α-methyl-γ-thiobutyro-lactone | |
| 100 (N = 24) | 152% (P < 0.03) |
| 175 (N = 30) | 174% (P < 0.001) |

[1]N is the number of animals used at the dose specified.
[2]P is the significance value calculated from the student's t-test.

TABLE 4

Convulsive Activity

| Compounds | CD$_{50}$ (mg/kg) |
|---|---|
| 3,3,4,4-Tetramethyl-2-pyrrolidinone | 32 |
| 5,5-Dimethyl-2-pyrrolidinone | 387 |
| 3-Ethyl-5,5-dimethyl-2-pyrrolidinone | 106 |
| 3,3-Diethyl-5,5-dimethyl-2-pyrrolidinone | 75 |

Parenteral administration is generally by injection, whether subcutaneously, intramuscularly, or intravenously. Injectables can be prepared in conventional forms, either as solutions or suspensions in liquid prior to injections or as emulsions. Suitable pharmaceutical carriers or excipients include water, saline, dextrose, glycerol, and the like. If desired, the pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet, and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain about 10–95% active ingredient with the remainder carrier, as a general rule.

For administration via suppository, conventional binders and carriers include, for example, polyalkylene glycols or triglycerides, and the suppositories generally contain active ingredient in the range of about 0.5–10%. Standard methods of formulating compounds for administration as pharmaceuticals can be found in Remington's Pharmaceutical Sciences, Mack Publishing Company, Easton, Pa., latest edition.

The amount of active compound to be administered depends on the subject being treated, the severity of the condition being treated, the manner of administration, and the judgment of the physician. However, an effective dose is in the range of about 10 mg to 2 grams/day per typical subject.

The following examples will further illustrate the invention in greater detail although it will be understood that the invention is not limited to these specific examples or the details described therein.

EXAMPLE 1

PREPARATION OF 3,3-DIETHYL-2-PYRROLIDINONE

Preparation of Ethyl 2-cyanomethyl-2-ethylbutanoate

A solution of ethyl 2-ethylbutyrate (21.60 g, 150 mmol) in THF (25 mL) was added dropwise to a solution of lithium diisopropylamide prepared by treating diisopropylamine (16.67 g, 165 mmol) in dry THF (150 mL) with butyllithium in hexanes (2.5M, 66 mL, 165 mmol) at −78° C. for 1 h in a nitrogen atmosphere. The resulting mixture was stirred at −78° C. for 1 h, then a solution of bromoacetonitrile (21.60 g, 180 mmol) in THF (50 mL) was introduced slowly over a period of 30 minutes (the reaction mixture starts getting darker as the addition progresses). The resulting dark mixture was stirred overnight (ca. 16 h) and allowed to warm from −78° C. to room temperature. The reaction was quenched by addition of HCl (1N, 250 mL) at 0° C. The layers were separated, and the aqueous phase was further extracted with ether (3×100 mL). The combined organic extract was washed sequentially with 75 mL portions of saturated $NaHCO_3$, water (several times), and brine, and dried over $MgSO_4$. The solvent was removed in vacuo to give 27.77 g of dark colored liquid. After two vacuum distillations, the nitrile (12.35 g, 45%) was obtained as a colorless liquid: bp 84°–85° C. (1.3 mmHg). Analytical sample was prepared by column chromatography over silica gel (hexanes-EtOAc, 19:1) followed by bulb-to-bulb distillation (pot temp. 80° C. (1 mmHg)).

Preparation of 3,3-Diethyl-2-pyrrolidinone

A pink solution of $CoCl_2.6H_2O$ (5.36 g, 22.5 mmol) and the nitrile, ethyl 2-cyanomethyl-2-ethylbutanoate (8.24 g, 45 mmol) in THF (158 mL, distilled) and $H_2O$ (79 mL) was stirred vigorously and cooled to 0° C. while $NaBH_4$ (8.55 g, 225 mmol) was added in portions over 30 minutes in a nitrogen atmosphere. The reaction was exothermic, producing a black precipitate and copious quantities of hydrogen. After stirring for 24 h at room temperature, 28% $NH_4OH$ (6 mL) was added, and the mixture stirred and refluxed for 72 h. After cooling the mixture was centrifuged, and the supernatant biphasic liquid was decanted. The sediment was washed with 15 mL of the same solvent mixture, and the combined supernatants were concentrated in vacuo to remove the bulk of THF. The aqueous residue was extracted with $CHCl_3$ (3×75 mL), the combined $CHCl_3$ layers were washed with brine (100 mL), and dried over $MgSO_4$. The solvent was removed in vacuo to give 6.20 g of a colorless viscous residue, which upon flash chromatography over silica gel (1% MeOH in $CHCl_3$-EtOAc, 1:1) afforded the lactam (4.42 g, 70%) as a colorless solid: mp 52°–53° C. (recrystalized from hexanes at −5° C.).

EXAMPLE 2

PREPARATION OF 3-ETHYL-3-METHYL-2-PYRROLIDINONE

Preparation of methyl 2-cyanomethyl-2-methylbutanoate

The reaction of methyl 2-methylbutyrate (13.34 g, 115 mmol) with bromoacetonitrile (16.56 g, 138 mmol) in the presence of lithium diisopropylamide (prepared by treating diisopropylamine (12.78 g, 126.5 mmol) with butyllithium in hexanes (2.5M, 50.6 mL, 126.5 mmol)) in THF (175 mL), as described above in the preparation of Example 1, gave 16.57 g of the crude product as a dark colored liquid. The crude product was vacuum distilled to give the nitrile (10.85 g, 61%) as a colorless liquid: bp 83°–85° C. (10 mmHg).

Preparation of 3-Ethyl-3-methyl-2-pyrrolidinone

The reaction of the nitrile, methyl 2-cyanomethyl-2-methylbutanoate (7.36 g, 47.5 mmol) with $NaBH_4$ (9.03 g, 237.5 mmol) and $CoCl_2.6H_2O$ (5.65 g, 23.75 mmol) in THF (166 mL) and $H_2O$ (83 mL), was carried out as described above in the preparation of Example 1. After the addition of $NaBH_4$, the reaction mixture was stirred for 48 h at room temperature, and subjected to the usual workup to give 5.79 g of the crude product as a colorless oily residue. Flash chromatography over silica gel (1% MeOH in $CHCl_3$-EtOAc, 1:1) afforded the lactam (4.30 g, 71%) as a colorless solid: mp 39°–40° C. (pentane at −5° C.).

EXAMPLE 3

PREPARATION OF 3-METHYL-3-(1-METHYLETHYL)-2-PYRROLIDINONE (i.e., 3-methyl-3-isopropyl-2-pyrrolidinone)

Preparation of methyl 2-cyanomethyl-2,3-dimethylbutanoate

Methyl 2-methylisovalerate (19.50 g, 150 mmol) was reacted with bromoacetonitrile (21.60 g, 180 mmol) in the presence of lithium diisopropylamide in THF (225 mL), as described above in the preparation of Example 1. The reaction gave 20.56 g of the crude product as a dark colored liquid. Methyl 2-methylisovalerate was prepared as described in Lion C, Dubois J E (1981) "Alkylation of some carbonyl compounds by tertiary alkyl groups. Utilization of the Friedel-Crafts reaction in the synthesis of sterically crowded esters and ketones" Tetrahedron, 37, 319–323.) Lithium diisopropylamide was prepared by treating diisopropylamine (16.67 g, 165 mmol) with butyllithium in hexanes (2.5M, 66 mL, 165 mmol).

Vacuum distillation of the crude product afforded 9.00 g of the slightly impure nitrile as a colorless oil: bp 89°–92° C. (2.2 mmHg). Column chromatography over silica gel (hexanes-EtOAc, 19:1) followed by bulb-to-bulb distillation (pot temp. 85° C. (1 mmHg)) gave the nitrile (7.55 g, 30%) as a colorless oil.

Preparation of 3-methyl-3-(1-methylethyl)-2-pyrrolidinone

The reaction of the nitrile, methyl 2-cyanomethyl-2,3-dimethylbutanoate (6.42 g, 38 mmol) with NaBH$_4$ (7.22 g, 190 mmol) and CoCl$_2$.6H$_2$O (4.52 g, 19 mmol) in THF (132 mL) and H$_2$O (66 mL), as described above in the preparation of Example 2, gave 4.35 g of the crude product as a colorless solid. Flash chromatography over silica gel (1% MeOH in CHCl$_3$-EtOAc, 1:1) afforded the lactam (3.77 g, 70%) as a colorless solid: mp 88°–90° C. (hexanes at –5° C.).

EXAMPLE 4

PREPARATION OF 3-PHENYLMETHYL-2-PYRROLIDINONE

Preparation of methyl 2-cyanomethyl-3-phenylpropanoate

A solution of lithium diisopropylamide was prepared by treating diisopropylamine (2.78 g, 27.5 mmol) in dry THF (35 mL) with butyllithium in hexanes (2.5M, 11 mL, 27.5 mmol) at 0° C. for 15 min in a nitrogen atmosphere. The solution was cooled to –78° C., and a solution of methyl 3-phenylpropionate (4.10 g, 25 mmol) in THF (10 mL) was added dropwise. The mixture was stirred at –78° C. for 45 min, then a solution of bromoacetonitrile (3.60 g, 30 mmol) in THF (10 mL) and HMPA (hexamethylphosphoramide) (2.2 mL, 12.5 mmol) was introduced slowly over a period of 15 min. The resulting dark mixture was stirred overnight (ca. 16 h) from –78° C. to room temperature. The reaction was quenched by addition of HCl (1N, 75 mL) at 0° C. The layers were separated and the aqueous phase was further extracted with ether (3×50 mL). The combined organic extract was washed sequentially with 75 mL portions of saturated NaHCO$_3$, water (several times), and brine, and dried over MgSO4. The solvent was removed in vacuo to give 5.70 g of dark colored liquid, which after column chromatography over silica gel (hexanes-EtOAc, 10:1) followed by shortpath distillation afforded the nitrile (1.70 g, 34%) as a colorless oil: bp 129°–131° C. (0.3 mmHg).

Preparation of 3-phenylmethyl-2-pyrrolidinone

The reaction of the nitrile, methyl 2-cyanomethyl-3-phenylpropanoate (3.05 g, 15 mmol) with NaBH$_4$ (2.85 g, 75 mmol) and CoCl$_2$.6H$_2$O (1.79 g, 7.5 mmol) in THF (54 mL) and H$_2$O (27 mL), as described above in the preparation of Example 2, gave 2.37 g of the crude product as a colorless solid. Flash chromatography over silica gel (1% MeOH in CHCl$_3$-EtOAc, 1:1) afforded the lactam (Menezes R. Smith M B (1988), supra) (1.48 g, 56%) as a colorless solid: mp 112°–113° C. (CH$_2$Cl$_2$-hexanes).

EXAMPLE 5

PREPARATION OF 3-METHYL-3-PHENYLMETHYL-2-PYRROLIDINONE

Preparation of ethyl 2-cyanomethyl-2-phenylmethylpropanoate

The reaction of ethyl 2-phenylmethylpropanoate (9.60 g, 50 mmol) with bromoacetonitrile (9.0 g, 75 mmol) in the presence of lithium diisopropylamide (prepared by treating diisopropylamine (6.06 g, 60 mmol) with butyllithium in hexanes (2.5M, 24 mL, 60 mmol)) in THF (150 mL) and HMPA (4.3 mL, 25 mmol), as described above in the preparation of Example 4, gave 11.95 g of the crude product as a pale yellow colored liquid. Ethyl 2-phenylmethylpropanoate was prepared as in Spencer R W, Tam T F, Thomas E, Robinson V J, Krantz A (1986) "Ynenol lactones: Synthesis and investigation of reactions relevant to their inactivation of serine proteases" J. Am. Chem. Soc., 108, 5589–5597. Flash chromatography over silica gel (hexanes-CH$_2$Cl$_2$, 3:2) afforded 7.86 g (68%) of the nitrile as a colorless viscous liquid. Analytical sample was prepared by bulb-to-bulb distillation (pot temp. 110°–115° C. (0.9 mmHg)).

Preparation of 3-methyl-3-phenylmethyl-2-pyrrolidinone

The reaction of the nitrile, ethyl 2-cyanomethyl-2-phenylmethylpropanoate (8.32 g, 36 mmol) with NaBH$_4$ (6.80 g, 180 mmol) and CoCl$_2$.6H$_2$O (4.28 g, 18 mmol) in THF (126 mL) and H$_2$O (63 mL), as described above in the preparation of Example 1, gave 6.78 g of the crude product as a pale brown colored solid. Flash chromatography over silica gel (1% MeOH in CHCl$_3$-EtOAc, 1:1) afforded the lactam (5.34 g, 78%) as a colorless solid: mp 89°–90° C. (CH$_2$Cl$_2$-hexanes).

EXAMPLE 6

PREPARATION OF 3-ETHYL-3-PHENYLMETHYL-2-PYRROLIDINONE

Preparation of methyl 2-cyanomethyl-2-phenylmethylbutanoate

Methyl 2-phenylmethylbutyrate (9.60 g, 50 mmol) was reacted with bromoacetonitrile (7.20 g, 60 mmol) in the presence of lithium diisopropylamide in THF (150 mL) and HMPA (4.3 mL, 25 mmol), as described above in the preparation of Example 4, to give 12.08 g of the crude product as a dark colored liquid. Methyl 2-phenylmethylbutyrate was prepared as in Colombo M, De Amici M, De Micheli C, Pitre D, Carrea G, Riva S (1991) "Chemoenzymatic synthesis of the enantiomers of iopanic acid" Tetrahedron:Asymmetry, 2, 1021–1030. Column chromatography over silica gel (hexanes-CH$_2$Cl$_2$, 3:2) afforded 5.98 g (52%) of the nitrile as a colorless viscous liquid. Analytical sample was prepared by bulb-to-bulb distillation (pot temp. 105° C. (0.5 mmHg)). Lithium diisopropylamide was prepared by treating diisopropylamine (5.56 g, 55 mmol) with butyllithium in hexanes (2.5M, 22 mL, 55 mmol).

Preparation of 3-ethyl-3-phenylmethyl-2-pyrrolidinone

The reaction of the nitrile, methyl 2-cyanomethyl-2-phenylmethylbutanoate (5.54 g, 24 mmol), with NaBH$_4$ (4.54 g, 120 mmol) and CoCl$_2$.6H$_2$O (2.86 g, 12 mmol) in THF (84 mL) and H$_2$O (42 mL), as described above in the preparation of Example 2, gave 4.95 g of the crude product as a slightly brown colored oily residue. Flash chromatography over silica gel (1% MeOH in CHCl$_3$-EtOAc, 1:1) afforded the lactam (3.69 g, 76%) as a colorless solid: mp 89°–90° C. (ether-hexanes at –5° C.).

EXAMPLE 7

PREPARATION OF 3-(1,1-DIMETHYLETHYL)-3-METHYL-2-PYRROLIDINONE (i.e., 3-tert-butyl-3-methyl-2-pyrrolidinone)

Preparation of methyl 2-(1,1-dimethylethyl)-2-methyl-4-pentenoate

A solution of lithium diisopropylamide was prepared by treating diisopropylamine (40.91 g, 405 mmol) in dry THF (350 mL) with butyllithium in hexanes (2.5M, 154.4 mL, 386 mmol) at 0° C. for 15 min in a nitrogen atmosphere. Then a solution of methyl 2,3,3-trimethylbutyrate (38.88 g, 270 mmol) in THF (30 mL) was added slowly, and the mixture was stirred. Methyl 2,3,3-trimethylbutyrate was prepared as in Quast H, Meichsner G, Seiferling B (1986) "Photochemical formation of methylenecyclopropane analogs. XII. Synthesis of 3,5,5-trialkyl-3,5-dihydro-4H-1,2,3-triazol-4-ones" Liebigs. Ann. Chem., 1891–1899. After 45 min. of stirring, the temperature of the mixture was reduced to −78° C. and a solution of allyl bromide (51.30 g, 424 mmol) in THF (20 mL) and HMPA (40.3 mL, 232 mmol) was added over a period of 15 min. Stirring was continued for 2 h at −78° C. and the system was allowed to warm to room temperature (ca. 6 h). The reaction was quenched by addition of HCl (3N, 300 mL) at 0° C. The layers were separated and the aqueous phase was further extracted with ether (3×150 mL). The combined organic extract was washed sequentially with 100 mL portions of water, 5% $Na_2S_2O_3$, saturated $NaHCO_3$, water, and brine, and dried over $MgSO_4$. The solvent was removed in vacuo to give 48.88 g of brown colored liquid, which upon two vacuum distillations, afforded olefinic ester (34.85 g, 70%) as a colorless liquid: bp 87°–89° C. (20 mmHg).

Preparation of methyl 2-(1,1-dimethylethyl)-2-methyl-4-oxobutanoate

A solution of the olefinic ester, methyl 2-(1,1-dimethylethyl)-2-methyl-4-pentenoate (2.76 g, 15 mmol), in dry $CH_2Cl_2$ (60 mL) was reacted with ozone at −78° C. When excess ozone was observed (blue coloration), nitrogen was bubbled through the solution, and $Ph_3P$ (5.90 g, 22.5 mmol) was added in one portion while stirring. The system was allowed to warm to room temperature (ca. 2 h) and stirred for 2 more hours. The solvent was removed in vacuo and the residue triturated with hexanes (150 mL). The precipitated $Ph_3PO$ (ca. 5.78 g) was filtered off and the filtrate concentrated in vacuo to give 2.80 g of the crude product as a colorless viscous residue. Flash chromatography over silica gel (hexanes-EtOAc, 19:1) afforded 2.12 g (76%) of the aldehyde as a colorless oil.

Preparation of methyl 2-(1,1-dimethylethyl)-2-methyl-4-oxobutanoate oxime

A solution of the aldehyde, methyl 2-(1,1-dimethylethyl)-2-methyl-4-oxobutanoate (2.05 g, 11 mmol) and $H_2NOH.HCl$ (1.15 g, 16.5 mmol) in dry pyridine (10 mL) was stirred at 60° C. for 4 h in a nitrogen atmosphere. After cooling the reaction mixture was poured into ice cold HCl (3N, 50 mL), and extracted with ether (3×40 mL). The combined ether extract was washed sequentially with 40 mL portions of saturated $NaHCO_3$, water, and brine, and dried over $MgSO_4$. The solvent was removed in vacuo to give 2.30 g of pale brown colored viscous liquid. Flash chromatography over silica gel (hexanes-EtOAc, 4:1) followed by bulb-to-bulb distillation (pot temp. 100°–105° C. (0.4 mmHg)) afforded the anti- and syn- oxime mixture (2.03 g, 92%) in the ratio of 58/42 as a colorless viscous liquid.

Preparation of 3-(1,1-dimethylethyl)-3-methyl-2-pyrrolidinone

A green solution of $NiCl_2.6H_2O$ (4.76 g, 20 mmol) and the oxime mixture, methyl 2-(1,1-dimethylethyl)-2-methyl-4-oxobutanoate oxime (anti- and syn-) (2.01 g, 10 mmol) in MeOH (100 mL) was stirred vigorously and cooled to −30° C. while $NaBH_4$ (3.80 g, 100 mmol) was added in portions over 30 minutes in a nitrogen atmosphere. The reaction was exothermic, producing a black precipitate and copious quantities of hydrogen. The cooling bath was removed and the mixture stirred for 1 h at room temperature. After removal of the solvent in vacuo, the black precipitate was dissolved in HCl (6N, 100 mL), then the acidic solution was made basic (pH 8–9) by the addition of 28% $NH_4OH$ (ca. 35 mL) at 0° C. The basic solution was extracted with $CH_2Cl_2$ (3×40 mL), the combined $CH_2Cl_2$ layers were washed with brine (50 mL), and dried over $MgSO_4$. The solvent was removed in vacuo to give the crude amino ester, methyl 4-amino-2-(1,1-dimethylethyl)-2-methylbutyrate, (1.62 g, 87%) as a colorless semisolid (IR (neat, NaCl): 3359 (br, NH), 1722 (C=O) cm−1).

To a stirred solution of the above aminoester (1.62 g, 8.66 mmol) in dry THF (18 mL), t-ButylOK (7.57 g, 67.6 mmol) was added at 0° C. in a nitrogen atmosphere. The cooling bath was removed and the mixture stirred for 16 h at room temperature. The reaction was quenched with saturated aqueous $NH_4Cl$ (50 mL), and the reaction mixture extracted with EtOAc (3×30 mL). The combined organic extract was washed with brine (30 mL) and dried over $MgSO_4$. The solvent was removed in vacuo to give 1.37 g of a colorless solid. Chromatography over silica gel (1% MeOH in $CHCl_3$-EtOAc, 1:1) afforded the lactam (1.19 g, 77%) as a colorless solid: mp 179°–181° C. (ether-hexanes).

EXAMPLE 8

PREPARATION OF 3-ETHYL-3-(1-METHYLETHYL)-2-PYRROLIDINONE (i.e. 3-ethyl-3-isopropyl-2-pyrrolidinone)

Preparation of methyl 2-ethyl-2-(1-methylethyl)-4-pentenoate

The reaction of methyl 2-ethyl-3-methylbutyrate (23.76 g, 165 mmol), prepared as in Lion C, Dubois J E (1981) supra., with allyl bromide (31.34 g, 259 mmol) in the presence of lithium diisopropylamide (prepared by treating diisopropylamine (25.05 g, 248 mmol) with butyllithium in hexanes (2.5M, 94.4 mL, 236 mmol)) in THF (330 mL) and HMPA (24.7 mL, 142 mmol), as described above in the preparation of Example 7, followed by the vacuum distillation of crude product afforded the pure olefinic ester (24.85 g, 82%) as a colorless liquid: bp 92°–94° C. (20 mmHg).

Preparation of methyl 2-ethyl-2-(1-methylethyl)-4-oxobutanoate

The reaction of the olefinic ester, methyl 2-ethyl-2-(1-methylethyl)-4-pentenoate (9.20 g, 50 mmol), with ozone in $CH_2Cl_2$ (200 mL) at −78° C., followed by the treatment of the resulting ozonide with $Ph_3P$ (19.65 g, 75 mmol) as described above in the preparation of Example 7, gave 14.36 g of an oily residue. Flash chromatography over silica gel (hexanes-EtOAc, 9:1) afforded the aldehyde (8.20 g, 88%) as a colorless oil.

Preparation of methyl 2-ethyl-2-(1-methylethyl)-4-oxobutanoate oxime

Methyl 2-ethyl-2-(1-methylethyl)-4-oxobutanoate (8.00 g, 43 mmol) was reacted with $H_2NOH.HCl$ (4.78 g, 68.8 mmol), as described above in Example 7 to give 8.20 g of slightly yellowish viscous liquid. Column chromatography over silica gel (hexanes-EtOAc, 4:1) followed by bulb-to-bulb distillation (pot temp. 110° C. (0.6 mmHg)) afforded the anti- and syn- oxime mixture (7.47 g, 86%) in the ratio of 60/40 as a colorless viscous liquid.

Preparation of 3-ethyl-3-(1-methylethyl)-2-pyrrolidinone

The reaction of the anti-/syn- oximes (7.04 g, 35 mmol) with $NaBH_4$ (13.30 g, 350 mmol) and $NiCl_2.6HO$ (16.66 g, 70 mmol) in MeOH (250 mL), as described above in Example 7 gave the crude methyl 4-amino-2-ethyl-2-(1-methylethyl)butyrate (7.59 g) as a dark colored liquid (IR (neat, NaCl): 3350 (br, NH), 1725 (C=O) cm−1).

The reaction of the above aminoester with t-ButylOK (15.29 g, 136.5 mmol) in THF (70 mL), as described above in the preparation of Example 7, gave 7.14 g of a dark colored semisolid. Flash chromatography over silica gel (1% MeOH in $CHCl_3$-EtOAc, 1:1) afforded the lactam (3.11 g, 57%, based on the oximes) as a colorless solid: mp 63°–64° C. (hexanes at −5° C.).

EXAMPLE 9

3,3-DIETHYL-2-PIPERIDINONE

Preparation of methyl 2,2-diethyl-5-hydroxypentanoate

To a stirred solution of methyl 2,2-diethyl-4-pentenoate (Canney D J, Holland K D, Levine J A, McKeon A C, Ferrendelli J A, Covey D F (1991), supra.)(5.10 g, 30 mmol) in dry THF (10 mL), was added $BH_3$.THF (1M, 12 mL, 12 mmol) slowly over a period of 15 min at 0° C. in a nitrogen atmosphere. After 2 h at 0° C., the reaction mixture was allowed to warm to room temperature (ca. 2 h). The reaction flask was immersed in an ice bath; water (5 mL) was added to destroy residual hydride, and the reaction mixture was oxidized by adding NaOH (3N, 3.2 mL) and then slowly adding 30% hydrogen peroxide (3.2 mL). After stirring for 1.5 h, the solution was poured into water (100 mL), and extracted with ether (3×50 mL). The combined ether extract was washed with 50 mL portions of water and brine, dried over MgSO4, and the solvent removed in vacuo to give 6.04 g of colorless oil. Column chromatography over silica gel (gradient elution, hexanes-EtOAc, 4:1 to 1:1) afforded the pure hydroxyester (2.79 g, 50%) as a colorless liquid.

Preparation of methyl 2,2-diethyl-5-oxopentanoate

To a well stirred mixture of the hydroxyester (1.88 g, 10 mmol), NaOAc (0.82 g, 10 mmol), and celite (1.88 g) in dry $CH_2Cl_2$ (50 mL), was added pyridinium chlorochromate (3.24 g, 15 mmol) at 0° C. in a nitrogen atmosphere. After 30 min at 0° C., the dark reaction mixture was stirred at room temperature for 2.5 h, and 100 mL of ether was added to it. Then it was filtered through a plug of silica gel and the solvent removed in vacuo to give 2.00 g of colorless viscous liquid. Column chromatography over silica gel (hexanes-EtOAc, 9:1) afforded the aldehyde (1.45 g, 78%) as a colorless liquid.

Preparation of methyl 2,2-diethyl-5-oxopentanoate oxime

The reaction of the aldehyde (1.40 g, 7.5 mmol) and $H_2NOH.HCl$ (0.83 g, 12 mmol), as described above in the preparation of Example 7, gave 1.58 g of colorless viscous oil. Flash chromatography over silica gel (hexanes-EtOAc, 17:3) followed by bulb-to-bulb distillation (pot temp. 105° C. (0.5 mmHg)) afforded the anti- and syn- oxime mixture (1.18 g, 78%) in the ratio of 56/44 as a colorless viscous material.

Preparation of 3,3-Diethyl-2-piperidinone

Reaction of the above oximes (1.01 g, 5 mmol) with $NaBH_4$ (1.90 g, 50 mmol) and $NiCl_2.6H_2O$ (2.38 g, 10 mmol) in MeOH (50 mL), as described above in the preparation of Example 7, gave crude methyl 5-amino-2,2-diethylpentanoate (0.96 g) as a pale yellow colored viscous residue (IR (neat, NaCl): 3364 (br, NH), 1728 (C=O) cm−1).

The reaction of the above aminoester with t-ButylOK (4.37 g, 39 mmol) in THF (10 mL), as described above in the preparation of Example 7, gave 0.99 g of the colorless viscous residue. Column chromatography over silica gel (1% MeOH in $CHCl_3$-EtOAc, 1:1) afforded the lactam (0.645 g, 83%) as a colorless solid: mp 62°–63° C. (hexanes at −5° C.). See: Baker J A, Harper J F (1967) supra.

EXAMPLE 10

REPARATION OF 3-PHENYLMETHYL-2-PIPERIDINONE

Preparation of 1,3-Diphenylmethyl-2-piperidinone

1-Phenylmethyl-2-piperidinone (See: Yamaguchi M, Hirao I (1985) "A direct synthesis of [(tert-butoxycarbonyl) methylidene]-azacycloalkanes from N-alkyllactams" J. Org. Chem., 50, 1975–1977) (3.40 g, 18 mmol) was reacted with benzyl bromide (4.84 g, 28.3 mmol) in the presence of lithium diisopropylamide (prepared by treating diisopropylamine (2.73 g, 27 mmol) with butyllithium in hexanes (2.5M, 10.3 mL, 25.7 mmol)) in THF (45 mL) and HMPA (2.7 mL, 15.5 mmol) as described above in the preparation of Example 7. After the addition of benzyl bromide, the reaction mixture was stirred for 2 h at −78° C., and then quenched with saturated $NH_4Cl$ (50 mL). The reaction mixture was extracted with ether (3×40 mL) and the combined ether extract washed with brine (40 mL) and dried over $MgSO_4$. The solvent was removed in vacuo, and the residue (8.40 g) thus obtained, was chromatographed over silica gel (hexanes-$CHCl_3$-EtOAC, 15:4:1 and then 7:2:1) to give the product lactam (3.14 g, 63%) as a colorless solid: mp 94°–95° C. ($CH_2Cl_2$-hexanes).

Preparation of 3-phenylmethyl-2-piperidinone

A solution of 1,3-diphenylmethyl-2-piperidinone (2.79 g, 10 mmol) in dry THF (25 mL) was added at −78° C. to a well stirred solution of Li metal (0.70 g, 100 mmol) in liquid $NH_3$ (200 mL). After 15 min, the cooling bath was removed, and the $NH_3$ was allowed to escape (ca. 2 h). The resulting colorless residue was treated with saturated $NH_4Cl$ (50 mL), and extracted with EtOAc (3×50 mL). The combined organic extract was washed with brine (25 mL), dried over MgSO4, and concentrated in vacuo to give 2.78 g of brown viscous residue. Flash chromatography over silica gel (1% MeOH in $CHCl_3$-EtOAc, 1:1) afforded the lactam (See: Rodriquez m, Heitz A, Martinez J (1992) supra) (0.87 g, 46% ) as a colorless solid: mp 120°–122° C. ($CH_2Cl_2$-hexanes).

EXAMPLE 11

PREPARATION OF 3-ETHYL-3-METHYL-2-PIPERIDINONE

Preparation of 3-ethyl-3-methyl-1-phenylmethyl-2-piperidinone

The reaction of 3-methyl-1-phenylmethyl-2-piperidinone (Meyers A I, Kunnen K B, Still W C (1987) "Conformational effects on the regiochemical metalation of C5–C13 N-benzyl lactams" J. Am. Chem. Soc., 109, 4405–4407.) (3.25 g, 16 mmol) with iodoethane (3.92 g, 25.1 mmol) in the presence of lithium diisopropylamide (prepared by treating diisopropylamine (2.42 g, 24 mmol) with butyllithium in hexanes (2.5M, 9.2 mL, 22.9 mmol)) in THF (45 mL) and HMPA (2.4 mL, 13.8 mmol) as described above in the preparation of Example 10, gave 5.90 g of pale yellow colored oil. Column chromatography over silica gel (hexanes-EtOAc, 9:1) afforded the product lactam (2.52 g, 68%) as a colorless viscous liquid. Analytical sample was prepared by bulb-to-bulb distillation (pot temp. 110°–115° C. (1 mmHg)).

Preparation of 3-ethyl-3-methyl-2-piperidinone

Li metal (0.63 g, 90 mmol) was added to a well stirred solution of 3-ethyl-3-methyl-1-phenylmethyl-2-piperidinone (2.08 g, 9 mmol) in dry THF (27 mL) and then liquid NH₃ (180 mL) was added slowly over a period of 5 min at −78° C. The cooling bath was removed and the reaction mixture stirred for 1 h at refluxing NH₃. Then the reaction mixture was heated for 5–10 min at 60° C. to evaporate NH₃ leaving a white residue which was treated carefully with water (50 mL) at 0° C., and the aqueous mixture extracted with CH₂Cl₂ (3×50 mL). The combined organic extract was washed with brine (50 mL), dried (MgSO4), and concentrated in vacuo to give 2.81 g of a colorless viscous residue. Flash chromatography over silica gel (1% MeOH in CHCl₃-EtOAc, 1:1) afforded the lactam (1.10 g, 87% ) as a colorless solid: mp 67°–69° C. (CH₂Cl₂-hexane).

EXAMPLE 12

PREPARATION OF 3-METHYL-3-PHENYLMETHYL-2-PIPERIDINONE

Preparation of 3-methyl-1,3-diphenylmethyl-2-piperidinone

The reaction of 3-methyl-1-phenylmethyl-2-piperidinone (3.65 g, 18 mmol) with benzyl bromide (4.84 g, 28.3 mmol) in the presence of lithium diisopropylamide (prepared by treating diisopropylamine (2.73 g, 27 mmol) with butyllithium in hexanes (2.5M, 10.3 mL, 25.7 mmol)) in THF (45 mL) and HMPA (2.7 mL, 15.5 mmol) as described above in the preparation of Example 10, gave 8.80 g of pale yellow colored oil. Column chromatography over silica gel (hexanes-EtOAc, 9:1) afforded the product lactam (3.72 g, 71%) as a colorless viscous residue. Analytical sample was prepared by bulb-to-bulb distillation (pot temp. 150°–155° C. (1.3 mmHg)).

Preparation of 3-methyl-3-phenylmethyl-2-piperidinone

The reaction of 3-methyl-1,3-diphenylmethyl-2-piperidinone (2.93 g, 10 mmol) with Li metal (0.70 g, 100 mmol) in THF (30 mL) and liquid NH₃ (200 mL), as described above in the preparation of Example 11, gave 3.18 g of a colorless viscous residue. Flash chromatography over silica gel (1% MeOH in CHCl₃-EtOAc, 1:1) afforded the lactam (1.75 g, 86% ) as a colorless solid: mp 76°–78° C. (ether-hexane).

EXAMPLE 13

PREPARATION OF 3-ETHYL-3-PHENYLMETHYL-2-PIPERIDINONE

Preparation of 3-ethyl-1,3-diphenylmethyl-2-piperidinone

The reaction of 3-ethyl-1-phenylmethyl-2-piperidinone (Yamaguchi M, Hirao I (1985) supra) (2.60 g, 12 mmol) with benzyl bromide (3.22 g, 18.8 mmol) in the presence of lithium diisopropylamide (prepared by treating diisopropylamine (1.82 g, 18 mmol) with butyllithium in hexanes (2.5M, 6.9 mL, 17.2 mmol)) in THF (30 mL) and HMPA (1.8 mL, 10.3 mmol) as described above in the preparation of Example 10, gave 5.64 g of pale yellow viscous liquid. Column chromatography over silica gel (hexanes-EtOAc, 9:1) afforded the product lactam (3.10 g, 84%) as a colorless solid: mp 88°–90° C. (CH₂Cl₂-hexane).

Preparation of 3-ethyl-3-phenylmethyl-2-piperidinone

The reaction of 3-ethyl-1,3-diphenylmethyl-2-piperidinone (2.76 g, 9 mmol) with Li metal (0.63 g, 90 mmol) in THF (27 mL) and liquid NH₃ (180 mL), as described above in the preparation of Example 11, gave 2.32 g of a colorless viscous residue. Flash chromatography over silica gel (1% MeOH in CHCl₃-EtOAc, 1:1) afforded the lactam (1.43 g, 73% ) as a colorless solid: mp 101°–102° C. (CH₂Cl₂-hexane).

EXAMPLE 14

ANTICONVULSANT TESTS

Pentylenetetrazol Seizure Threshold Test (PTZ)

Anticonvulsant screening was accomplished by methods based on those of Swinyard and Woodhead using female CF-1 strain mice. (Swinyard E A, Woodhead J H (1982) "Experimental detection, quantification, and evaluation of anticonvulsants" Antiepileptic Drugs, Woodbury D M, Penry J K, Pippenger C E, Eds., Raven Press, New York, N.Y., 2nd Edition, pp 111–126.) Test compounds were dissolved in 30% polyethylene glycol and given by intraperitoneal (ip) injections in a volume of 0.01 mL/g of body weight. Following a 30 minute period during which no convulsant activity was observed, pentylenetetrazol (85 mg/kg; CD97) prepared as a 0.85% solution in 0.9% NaCl was injected ip into mice. The animals were placed in isolation cages and observed for the next 30 minutes for the presence or absence of a seizure. A threshold convulsion is defined as one episode of clonic spasms that persists for at least a 5-sec period. Absence of a threshold convulsion during the 30 minutes period of observation was taken as the endpoint and indicates that the substance has the ability to elevate the threshold of the pentylenetetrazol seizure. Results of the PTZ test with representative compounds of this invention are provided in Table 2.

Convulsant activity of test compounds is assessed by monitoring injected mice by monitoring seizures by observing for the onset of myoclonic twitches, generalized clonic seizures and tonic seizures.

Maximal Electroshock Seizure Test (MES)

Test compounds were dissolved in 30% polyethylene glycol and given by intraperitoneal (ip) injections in a volume of 0.01 mL/g of body weight. Following a 30 minute period during which no convulsant activity was observed, a drop of 0.9% sodium chloride was applied to the eyes of each animal. Corneal electrodes were applied to the eyes, and an electrical stimulus consisting of a 60-Hz alternating current of 50 mA was delivered for 0.2 sec. The animals were held by hand and released at the time of stimulation for observation of the seizure. Abolition of the hindleg tonic extension component was taken as the endpoint for this test. The tonic component was considered abolished if the hindleg tonic extension did not exceed 90° with the plane of the body. Results of the MES test with representative compounds of this invention are provided in Table 2.

EXAMPLE 15

ANXIOLYTIC TEST

A modification of the plus-maze test (Lister R G (1987) "The use of a plus-maze to measure anxiety in the mouse" Psychopharmacology, 92, 180–185.) was used to measure the anxiolytic activity of the compounds of this invention in mice. The plus-maze apparatus used in the test consisted of four 30 cm×5 cm arms, two of which were enclosed by 16 cm high walls while the other two were unwalled. The four arms radiated out from a 5×5 cm central platform. The entire maze was elevated 34 cm on legs. The floor parts of the maze were made of wood painted black. The walls were clear plexiglass.

Male mice of the NIH Swiss strain are used in the test which is carried out in a room with no distractions. Test compounds were dissolved in 30% polyethylene glycol and given by intraperitoneal (ip) injections in a volume of 0.01 mL/g of body weight. Following a 30 minute period during which no convulsant activity was observed, each mouse was placed in the center of the plus-maze, facing an open arm. During each 5 minute test, the number of entries to open arms and closed arms and the amount of time spent on each were recorded. A mouse has entered an arm when all four feet are on the arm. Each mouse was used only once. The anxiolytic dose of a test compound is that dose which causes a significant increase in the amount of time the test mouse spends in the open arms of the plus-maze in comparison to the amount of time a control mouse not receiving a test compound spends in the open arms of the maze. Results of this test with representative compounds of this invention are provided in Table 3.

EXAMPLE 16

NEUROTOXICITY TEST

Rotorod Test for Toxicity

This test is used in mice to assess neurotoxicity. Mice were placed on a 1 in. diameter rod, which rotates at 6 rpm, and tested for maintenance of their equilibrium for 10 min. All mice were pre-tested before a test substance is given. Test compounds are dissolved in 30% polyethylene glycol and given by intraperitoneal (ip) injections in a volume of 0.01 mL/g of body weight. Following a 30 min. period during which no convulsant activity was observed, mice were put back on the rotorod for 10 min. Neurological deficit (toxicity) is indicated if the test compound caused a mouse to fall from the rotating rod twice during the 10 minute testing period. This test also measures sedative effect of the compound tested. See, for example, EP application 151,964 published Aug. 21, 1985. Results of this test as $TD_{50}$ in mg/kg for representative compounds of this invention are provided in Table 2.

EXAMPLE 17

$GABA_A$ RECEPTOR ELECTROPHYSIOLOGY TEST

Hippocampal Cell Culture Methods

Under halothane anaesthesia, 1 day old female Sprague-Dawley rats were sacrificed by rapid decapitation and the hippocampi were dissected, minced and incubated in 3 mL of Leibovitz's L-15 containing 1 mg/mL papain and 0.2 mg/mL bovine serum albumin (BSA) for 20 min. at 37° C. The papain solution was removed and the hippocampi were triturated with pasteur pipettes in growth medium. The resulting suspension was centrifuged through 2 mL of medium containing 10 mg/mL trypsin inhibitor and 10 mg/mL BSA. The cells were resuspended into growth medium and plated, 2.5×105 cells/dish, on a monolayer of cortical glial cells in 35 mm plastic culture dishes. The culture dishes were pretreated with poly-L-lysine followed by plating of glial cells harvested from the cortices of 2–6 day postnatal rats four days prior to neuron plating. Growth medium for hippocampal cells was minimum essential medium, without glutamine, supplemented with 10% NuSerum, penicillin (20 U/mL) and streptomycin (20 mg/mL). On the third day after plating, glial growth was inhibited with 15 mg/mL fluorodeoxyuridine and 35 mg/mL uridine. Neurons were used for electrophysiology 7–21 days after plating.

Electrophysiological Recording

Experiments were performed on the stage of an inverted microscope utilizing phase contrast optics. Patch pipettes made from borosilicate glass (1.2 mm diameter, thin wall) with a two-stage vertical puller were fire-polished with a microforge and filled with an intracellular solution containing: 130 mM CsCl, 10 mM TEA-Cl, 10 mM HEPES, 1.1 mM EGTA, 2 mM Mg-ATP, 2 mM QX-314 (see below) and 5.5 mM glucose (pH 7.2). Electrode resistances ranged from 4–8 MΩ. A Ag/AgCl wire connected the electrode to the headstage of a patch clamp amplifier. The reference electrode was a Ag/AgCl wire embedded in agar and immersed in the recording chamber. Junction potentials were routinely corrected for using the amplifier offset mechanism.

Medium in the culture dishes was replaced with an extracellular solution containing: 140 mM NaCl, 3 mM KCl, 10 mM HEPES, 5 mm $MgCl_2$, and 5.5 mM glucose. Neurons were recorded using the whole cell configuration of the patch clamp technique, (Hamil P O, Marty A, Neher E, Sakmann B, Sakmann J F (1981) "Improved patch-clamp techniques for high resolution current recordings from cells and cell-free membrane patches" Pfluegers Arch., 391, 85–100.) and the neuronal membrane was clamped to a potential of 130 mV. The series resistance of the electrodes, typically 5–20 MΩ, was partially compensated following electronic cancellation of transient capacitative currents.

Spatial voltage clamp was improved by reducing intrinsic membrane conductances and synaptic activity in the dish. Intracellular cesium (Cs+) and TEA eliminate K+ conductances. Lidocaine N-ethylbromide (QX-314) eliminates the voltage-dependent Na+ conductance and prevents action potential generation at depolarized potentials. Finally, recording in a Ca2+-free, high magnesium solution eliminates Ca2+ currents and reduces synaptic activity.

Membrane currents were sampled at 1 kHz, digitized and stored on a personal computer for off-line analysis. The pCLAMP software (Axon Instruments) was utilized to run all experimental protocols and to acquire and analyze data files.

Drug Application

A method for even and fast local solution exchange was used. Drugs were applied to the neuron through large bore (340 mm) pipettes ("flow tubes") positioned approximately 50 mm from the cell. GABA and/or drugs dissolved in extracellular solution flow in a gravity-driven manner through solenoid valves, each connected individually to a flow tube. A linear array of six flow tubes allowed the recording of responses to multiple drugs or multiple concentrations of a drug to the same cell. Once the proper flow tube was positioned with a micromanipulator opposite the neuron, the valve was triggered to open by the computer. Drug application times were typically 400 to 1000 msec. The 35 mm dish was fitted with an insert to reduce extracellular volume to less than 1 mL and was perfused with fresh extracellular solution at a rate of 1.5 mL/min to prevent accumulation of drug. Results of this test for 1 mM concentrations of representative drugs of this invention, expressed as percent of control response to 3 µM GABA, are provided in Table 1.

Scheme 1
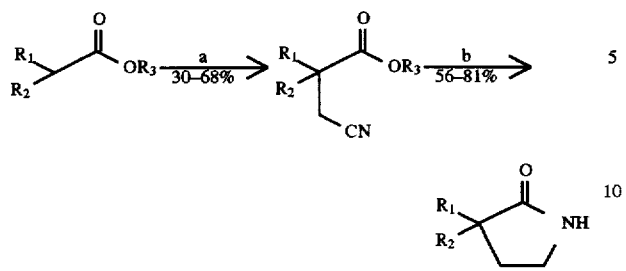
(a) LDA, BrCH$_2$CN in THF; (b) CoCl$_2$.6H$_2$O, NaBH$_4$ in THF—H$_2$O
Scheme 2
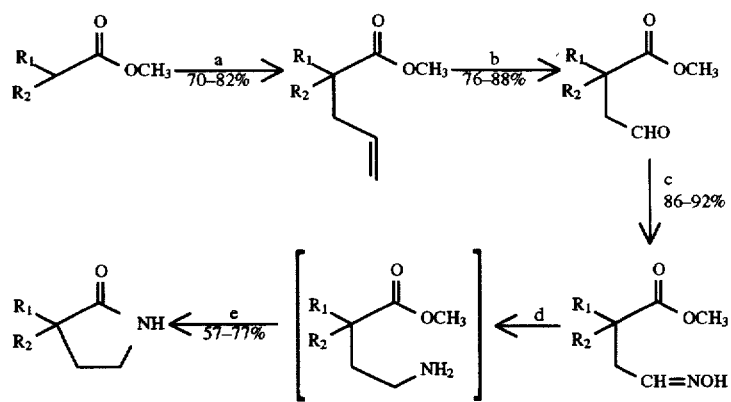
(a) LDA, allyl bromide in THF-HMPA; (b) i: O$_3$ in CH$_2$Cl$_2$; ii: Ph$_3$P; (c) H$_2$NOH.HCl in C$_6$H$_5$N; (d) NiCl$_2$.6H$_2$O, NaBH$_4$ in MeOH; (e) t-BuOK in THF
Scheme 3
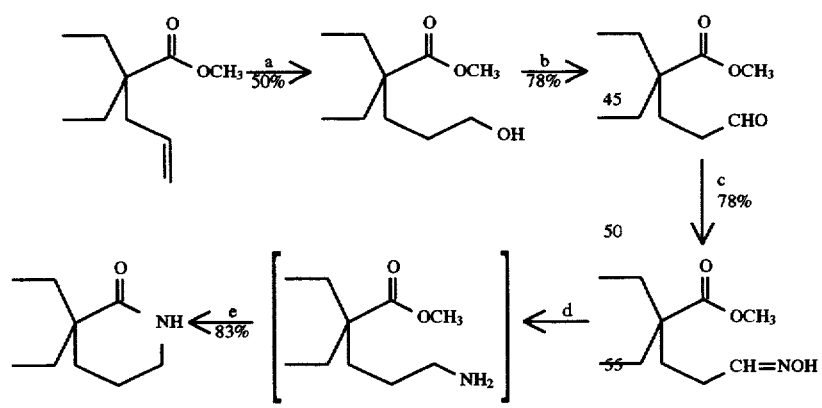
(a) i: BH$_3$.THF in THF; ii: H$_2$O$_2$—NaOH; (b) PCC, NaOAc, Celite in CH$_2$Cl$_2$; (c) H$_2$NOH.HCl in C$_6$H$_5$N; (d) NiCl$_2$.6H$_2$O, NaBH$_4$ in MeOH; (e) t-BuOK in THF

Scheme 4

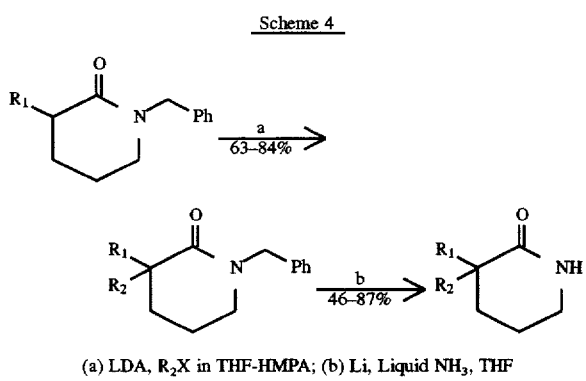

(a) LDA, R$_2$X in THF-HMPA; (b) Li, Liquid NH$_3$, THF

We claim:

1. A method for enhancing GABA-induced chloride currents at the GABA receptor/ionophore complex in a mammal which comprises the step of administering to said mammal a pharmaceutical composition having anticonvulsant or anxiolytic activity which comprises a pharmaceutical carrier and one or more of the anticonvulsant or anxiolytic compounds selected from the group consisting of the compounds of formula:

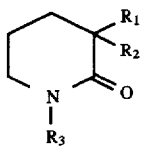

and pharmaceutically acceptable salts thereof wherein:

R$_1$, R$_2$, and R$_3$ are selected from the group consisting of a hydrogen, an optionally substituted alkyl or alkenyl group, and a phenylmethyl group wherein at least one of R$_1$ or R$_2$ is a phenylmethyl group; and wherein said compound or mixture of compounds is present in said composition in an amount effective for preventing or ameliorating convulsant seizures or anxiety in said mammal to which it is administered.

2. The method according to claim 1 wherein the other of R$_1$ or R$_2$ is an alkyl group.

3. The method according to claim 2 wherein the other of R$_1$ or R$_2$ is a C1–C4 alkyl group.

4. The method according to claim 1 wherein R$_3$ is a hydrogen.

5. The method according to claim 1 wherein said anticonvulsant or anxiolytic compounds are selected from the group consisting of 3-ethyl-3-phenylmethyl-2-piperidinone, 3-methyl-3-phenylmethyl-2-piperidinone, 3-phenylmethyl-2-piperidinone and pharmaceutically acceptable salts thereof.

6. A method for treating convulsant seizures in a mammal which comprises the step of administering to said mammal a pharmaceutical composition having anticonvulsant or anxiolytic activity which comprises a pharmaceutical carrier and one or more of the anticonvulsant or anxiolytic compounds selected from the group consisting of the compounds of formula:

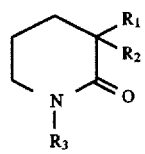

and pharmaceutically acceptable salts thereof wherein:

R$_1$, R$_2$, and R$_3$ are selected from the group consisting of a hydrogen, an optionally substituted alkyl or alkenyl group, and a phenylmethyl group wherein at least one of R$_1$ or R$_2$ is a phenylmethyl group; and wherein said compound or mixture of compounds is present in said composition in an amount effective for preventing or ameliorating convulsant seizures or anxiety in said mammal to which it is administered.

7. The method according to claim 6 wherein the other of R$_1$ or R$_2$ is an alkyl group.

8. The method according to claim 7 wherein the other of R$_1$ or R$_2$ is a C1–C4 alkyl group.

9. The method according to claim 6 wherein R$_3$ is a hydrogen.

10. The method according to claim 6 wherein said anticonvulsant or anxiolytic compounds are selected from the group consisting of 3-ethyl-3-phenylmethyl-2-piperidinone, 3-methyl-3-phenylmethyl-2-piperidinone, 3-phenylmethyl-2-piperidinone and pharmaceutically acceptable salts thereof.

11. A method for treating anxiety in a mammal which comprises the step of administering to said mammal a pharmaceutical composition having anticonvulsant or anxiolytic activity which comprises a pharmaceutical carrier and one or more of the anticonvulsant or anxiolytic compounds selected from the group consisting of the compounds of formula:

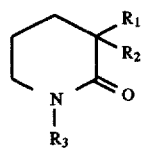

and pharmaceutically acceptable salts thereof wherein:

R$_1$, R$_2$, and R$_3$ are selected from the group consisting of a hydrogen, an optionally substituted alkyl or alkenyl group, and a phenylmethyl group wherein at least one of R$_1$ or R$_2$ is a phenylmethyl group; and wherein said compound or mixture of compounds is present in said composition in an amount effective for preventing or ameliorating convulsant seizures or anxiety in said mammal to which it is administered.

12. The method according to claim 11 wherein the other of R$_1$ or R$_2$ is an alkyl group.

13. The method according to claim 12 wherein the other of R$_1$ or R$_2$ is a C1–C4 alkyl group.

14. The method according to claim 11 wherein R$_3$ is a hydrogen.

15. The method according to claim 11 wherein said anticonvulsant or anxiolytic compounds are selected from the group consisting of 3-ethyl-3-phenylmethyl-2-piperidinone, 3-methyl-3-phenylmethyl-2-piperidinone, 3-phenylmethyl-2-piperidinone and pharmaceutically acceptable salts thereof.

16. A pharmaceutical composition having anticonvulsant or anxiolytic activity which comprises a pharmaceutical carrier and one or more anticonvulsant or anxiolytic compounds having the formula:

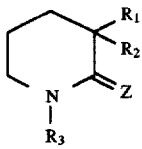

and pharmaceutically acceptable salts thereof wherein:

Z is an oxygen or a sulfur atom;

$R_1$ and $R_2$ are selected from the group consisting of an optionally substituted alkyl, an optionally substituted alkenyl group, and an optionally substituted phenylmethyl group wherein at least one of $R_1$ or $R_2$ is a phenylmethyl group; and $R_3$ is selected from the group consisting of a hydrogen, an optionally substituted alkyl or alkenyl group, and a phenylmethyl group with the exception that $R_3$ is not substituted with a mercapto or a thioalkoxy group; and wherein said compound or mixture of compounds is present in said composition in an amount effective for preventing or ameliorating convulsant seizures or anxiety in a mammal to which it is administered.

17. The composition of claim 16 wherein Z is an oxygen atom.

18. The composition of claim 17 wherein said anticonvulsant or anxiolytic compounds are selected from the group consisting of 3-ethyl-3-phenylmethyl-2-piperidinone, 3-methyl-3-phenylmethyl-2-piperidinone, 3-phenylmethyl-2-piperidinone and pharmaceutically acceptable salts thereof.

19. The composition of claim 17 wherein said anticonvulsant or anxiolytic compounds are selected from the group consisting of 3-ethyl-3-phenylmethyl-2-piperidinone, 3-methyl-3-phenylmethyl-2-piperidinone, and pharmaceutically acceptable salts thereof.

20. A method for enhancing GABA-induced chloride currents at the GABA receptor/ionophore complex in a mammal which comprises the step of administering to said mammal a pharmaceutical composition of claim 16.

21. A method for treating convulsant seizures in a mammal which comprises the step of administering to said mammal a pharmaceutical composition of claim 16.

22. A method for treating anxiety in a mammal which comprises the step of administering to said mammal a pharmaceutical composition of claim 16.

23. A pharmaceutical composition having anticonvulsant or anxiolytic activity which comprises a pharmaceutical carrier and one or more anticonvulsant or anxiolytic compounds having the formula:

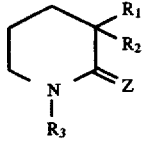

and pharmaceutically acceptable salts thereof wherein:

Z is an oxygen of a sulfur atom;

$R_1$ and $R_2$ are selected from the group consisting of a C1–C4 fluoroalkyl group or a C-2 to C-4 fluoroalkenyl group;

$R_3$ is selected from the group consisting of a hydrogen, an optionally substituted alkyl or alkenyl group, and a phenylmethyl group;

with the exception that $R_3$ is not substituted with a mercapto or a thioalkoxy group said compound or mixture of compounds present in said composition in an amount effective for preventing or ameliorating convulsant seizures or anxiety in a mammal to which it is administered.

24. The compound of claim 23 wherein Z is an oxygen atom.

25. The composition of claim 23 wherein $R_3$ is hydrogen.

26. A method for enhancing GABA-induced chloride currents at the GABA receptor/ionophore complex in a mammal which comprises the step of administering to said mammal a pharmaceutical composition of claim 23.

27. A method for treating convulsant seizures in a mammal which comprises the step of administering to said mammal a pharmaceutical composition of claim 23.

28. A method for treating anxiety in a mammal which comprises the step of administering to said mammal a pharmaceutical composition of claim 23.

29. A method for enhancing GABA-induced chloride currents at the GABA receptor/ionophore complex in a mammal which comprises the step of administering to said mammal a pharmaceutical composition having anticonvulsant or anxiolytic activity which comprises a pharmaceutical carrier and one or more of the anticonvulsant or anxiolytic compounds selected from the group consisting of the compounds of formula:

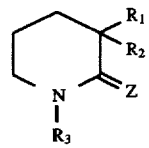

and pharmaceutically acceptable salts thereof wherein:

Z is an oxygen or a sulfur atom;

$R_1$, and $R_2$ are selected from the group consisting of an optionally substituted alkyl or optionally substituted alkenyl groups wherein $R_1$ and $R_2$ are not both methyl groups or both ethyl groups; and $R_3$ is selected from the group consisting of optionally substituted alkyl, optionally substituted alkenyl groups, or optionally substituted phenyl methyl groups; and wherein said compound or mixture of compounds is present in said composition in an amount effective for preventing or ameliorating convulsant seizures or anxiety in said mammal to which it is administered.

30. The method of claim 29 wherein Z is an oxygen atom.

31. The method of claim 30 wherein $R_1$ and $R_2$ are optionally substituted alkyl groups.

32. The method of claim 30 wherein $R_1$ and $R_2$ are C2–C4 alkyl groups.

33. The method of claim 30 wherein $R_3$ is a hydrogen.

34. A method for treating convulsant seizures in a mammal which comprises the step of administering to said mammal a pharmaceutical composition having anticonvulsant activity which comprises a pharmaceutical carrier and one or more of the anticonvulsant compounds selected from the group consisting of the compounds of formula:

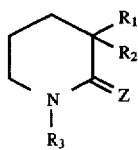

and pharmaceutically acceptable salts thereof wherein:

Z is an oxygen or a sulfur atom;

R$_1$, and R$_2$ are selected from the group consisting of an optionally substituted alkyl or optionally substituted alkenyl groups wherein R$_1$ and R$_2$ are not both methyl groups; and R$_3$ is selected from the group consisting of optionally substituted alkyl, optionally substituted alkenyl groups, or optionally substituted phenyl methyl groups; and wherein said compound or mixture of compounds is present in said composition in an amount effective for preventing or ameliorating convulsant seizures in said mammal to which it is administered.

35. The method of claim 34 wherein Z is an oxygen atom.

36. The method of claim 35 wherein R$_1$ and R$_2$ are optionally substituted alkyl groups.

37. The method of claim 34 wherein R$_1$ and R$_2$ are C2–C4 alkyl groups.

38. The method of claim 37 wherein R$_3$ is a hydrogen.

39. The method of claim 35 wherein said anticonvulsant compounds are selected from the group consisting of 3,3-diethyl-2-piperidinone and pharmaceutically acceptable salts thereof.

40. A method for treating anxiety in a mammal which comprises the step of administering to said mammal a pharmaceutical composition having anticonvulsant or anxiolytic activity which comprises a pharmaceutical carrier and one or more of the anticonvulsant or anxiolytic compounds selected from the group consisting of the compounds of formula:

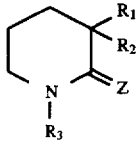

and pharmaceutically acceptable salts thereof wherein:

Z is an oxygen atom or a sulfur atom;

R$_1$ and R$_2$ are selected from the group consisting of an optionally substituted alkyl or optionally substituted alkenyl groups wherein R$_1$ and R$_2$ are not both methyl groups or both ethyl groups; and R$_3$ is selected from the group consisting of optionally substituted alkyl, optionally substituted alkenyl groups, or optionally substituted phenyl methyl groups; and wherein said compound or mixture of compounds is present in said composition in an amount effective for preventing or ameliorating convulsant seizures or anxiety in said mammal to which it is administered.

41. The method of claim 40 wherein Z is an oxygen atom.

42. The method of claim 41 wherein R$_1$ and R$_2$ are optionally substituted alkyl groups.

43. The method of claim 41 wherein R$_1$ and R$_2$ are C2–C4 alkyl groups.

44. The method of claim 41 wherein R$_3$ is a hydrogen.

45. A pharmaceutical composition having anticonvulsant or anxiolytic activity which comprises a pharmaceutical carrier and one or more anticonvulsant or anxiolytic compounds having the formula:

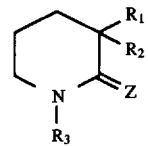

and pharmaceutically acceptable salts thereof wherein:

Z is an oxygen or a sulfur atom;

R$_1$ and R$_2$ are selected from the group consisting of an optionally substituted alkyl or an optionally substituted alkenyl group wherein R$_1$ and R$_2$ are not both methyl groups or both ethyl groups; and R$_3$ is selected from the group consisting of a hydrogen, an optionally substituted alkyl or alkenyl group, and a phenylmethyl group;

said compound or mixture of compounds present in said composition in an amount effective for preventing or ameliorating convulsant seizures or anxiety in a mammal.

46. The composition of claim 45 wherein Z is an oxygen atom.

47. A method for enhancing GABA-induced chloride currents at the GABA receptor/ionophore complex in a mammal which comprises the step of administering to said mammal a pharmaceutical composition of claim 45.

48. A method for treating convulsant seizures in a mammal which comprises the step of administering to said mammal a pharmaceutical composition of claim 45.

49. A method for treating anxiety in a mammal which comprises the step of administering to said mammal a pharmaceutical composition of claim 45.

* * * * *